US007399901B2

(12) United States Patent
Malissen et al.

(10) Patent No.: US 7,399,901 B2
(45) Date of Patent: Jul. 15, 2008

(54) MUTATED GENE CODING FOR A LAT PROTEIN AND THE BIOLOGICAL APPLICATIONS THEREOF

(75) Inventors: Marie Malissen, Marseilles (FR); Bernard Malissen, Marseilles (FR); Enrique Aguado Vidal, Murcia (ES)

(73) Assignee: Institut National de la Sante et de la Recherche Medicale (Inserm), Paris (FR)

( * ) Notice: Subject to any disclaimer, the term of this patent is extended or adjusted under 35 U.S.C. 154(b) by 149 days.

(21) Appl. No.: 10/502,332

(22) PCT Filed: Feb. 14, 2003

(86) PCT No.: PCT/IB03/01044

§ 371 (c)(1),
(2), (4) Date: Jul. 23, 2004

(87) PCT Pub. No.: WO03/068968

PCT Pub. Date: Aug. 21, 2003

(65) Prior Publication Data

US 2005/0114914 A1 May 26, 2005

Related U.S. Application Data

(60) Provisional application No. 60/356,136, filed on Feb. 14, 2002.

(30) Foreign Application Priority Data

Mar. 11, 2002 (EP) .................................. 02290610

(51) Int. Cl.
*A01K 67/027* (2006.01)
*C12N 15/00* (2006.01)
*C12N 15/87* (2006.01)

(52) U.S. Cl. ............................. 800/18; 800/21; 800/22; 435/320.1; 435/463

(58) Field of Classification Search ................. 800/3, 800/18, 21, 22, 25; 435/455, 463, 320.1, 435/325
See application file for complete search history.

(56) References Cited

FOREIGN PATENT DOCUMENTS

WO    WO 99/32627    7/1999

OTHER PUBLICATIONS

Sommers et al., J. Exp. Med, 194(2): 135-142 (Jul. 16, 2001).*
Zhang et al. Immunity, 10:323-332, Mar. 1999.*
Kappell et al. Current Opinion in Biotechnology 3:548-553 (1992).*
Mullins et al. Hypertension 22:630-633 (1993).*
Houdebine. J. Biotech. 34:269-287 (1994).*
Mullins et al. J. Clin. Invest. 97:1557-1560 (1996).*
Cameron. Molec. Biol. 7:253-265 (1997).*
Sigmund. Arterioscler. Throm. Vasc. Biol. 20:1425-1429 (2000).*
Niemann. Transg. Res. 7:73-75 (1998).*
Seffernick et al. J. Bacteriol. 183(8):2405-2410, 2001.*
Witkowski et al. Biochemistry 38:11643-11650, 1999.*
Moreadith et al. J. of Mol. Med. 75:208-216 (1997).*
The Free Dictionary by Farlex [online], term "corresponding" [retrieved on Jul. 31, 2006]. Retrieved from the Internet,:URL: http://www.thefreedictionary.com/corresponding?p>).*
Kuby, Immunology, 2nd edition, 1994, ed. W.H. Freeman and Company, p. 311.*
Encyclopaedia Britannica. Retrieved Jan. 22, 2007, from Encyclopaedia Britannica Online: http://www.search.eb.com/eb/article-9105980.*
Mullins. Nature, vol. 344, 541-544, 1990.*
Hammer. Cell, vol. 63, 1099-1112, 1990.*
Mullins, EMBO J., vol. 8, pp. 4065-4072, 1989.*
Taurog, Jour. Immunol., vol. 141, pp. 4020-4023, 1988.*
Charreau et al. Transgenic Research, 5:223-234 (1996).*
Genton et al., The Journal of Immunology, 2006, 177:2285-2293 "The Th2 lymphoproliferation developing in LatY136F mutant mice triggers polyclonal B cell activation and systemic autoimmunity".
Aguardo et al, "Induction of T Helper Type 2 Immunity by a Point Mutation in the LAT Adaptor", Science, vol. 296, No. 5575, 2002, pp. 2036-2040.
Sommers et al, "A LAT Mutation That Inhibits T Cell Development Yet Induces Lymphoproliferatiion", Science, vol. 296, No. 5575, 2002, pp. 2040-2043.
Samelson et al, "Studies on the Adapter Molecule LAT", Cold Spring Symposia on Quantitative Biology, Biological Laboratory, Cold Spring Harbor, NY, US, No. 64, 1999, pp. 259-263.
Lin et al, "Identification of the Minimal Tyrosine Residues Required for Linker for Activation of T Cell Function", Journal of Biological Chemistry, vol. 276, No. 31, Aug. 3, 2001, pp. 29588-29595.
Zhang et al, "Association of Grb2, Gads, and Phospholipase Cγ1 with Phosphorylated LAT Tyrosine Residues", Journal of Biological Chemistry, vol. 275, No. 30, Jul. 28, 2000, pp. 23355-23361.
Zhang et al, "Essential Role of LAT in T Cell Development", Immunity, vol. 10, No. 3, Mar. 1999, pp. 323-332.
Saitoh et al, "LAT Is Essential for FceRI-Medicated Mast Cell Activation", Immunity, vol. 12, No. 5, May 2000, pp. 525-535.

* cited by examiner

*Primary Examiner*—Thaian N Ton
(74) *Attorney, Agent, or Firm*—Nixon & Vanderhye P.C.

(57) ABSTRACT

The present invention relates to a mutated gene coding for a mutant LAT protein leading to exaggerated $T_H2$ differentiation. The invention relates to biological structures containing the mutant, particularly non-human LAT gene, mutated animals, plasmids, chromosomal DNAs, embryos comprising the mutated gene, and applications thereof. The invention further relates to screening methods for drugs useful for treatment against asthma and allergy. Otherwise, the invention relates to methods for producing IgE antibodies.

15 Claims, 11 Drawing Sheets

US 7,399,901 B2

MUTATED GENE CODING FOR A LAT PROTEIN AND THE BIOLOGICAL APPLICATIONS THEREOF

This application is the US national phase of international application PCT/IB03/01044 filed 14 Feb. 2003 which designated the U.S. and claims benefit of U.S. 60/356,136, dated 14 Feb. 2002 and EP 02290610.1, dated 11 Mar. 2002, the entire content of each of which is hereby incorporated by reference.

The present invention relates to a mutated gene coding for two mutant LAT proteins leading to an exaggerated $T_H2$ cell differentiation. The invention relates to biological structures containing said mutant, particularly, non-human LAT gene mutated animals, cell cultures, plasmids, chromosomal DNAs, embryos comprising said mutated gene, and applications thereof. The invention further relates to screening methods for drug useful for treatment against asthma, allergy and any pathological immune responses involving $T_H2$ cells. The invention also relates to method for producing IgE antibodies.

BACKGROUND ART

A key event in the pathogenesis is the production of antibodies of the IgE class. Hypergammaglobulinemia E results from loss of immunoregulation. More specifically, T lymphocyte abnormalities have been reported in a number of pathologic hyper IgE conditions and are the object of much research aiming at developing pharmaceutical compounds that will prevent atopic allergy and asthma.

TCR recognize peptide fragments bound to major histocompatibility complex (MHC) molecules and relay this information to the interior of the T cell via adapter proteins. One of these, the adapter LAT (Linker for Activation of T cells), coordinates the assembly of signaling complexes through multiple tyrosine residues within its intracytoplasmic segment. Upon TCR-induced phosphorylation, each of these tyrosine residues manifests some specialization in the signaling proteins it recruits. Studies on cell lines showed that mutation of tyrosine 136 (Y136) selectively eliminates binding of phospholipase Cγ1 (PLC-γ1) whereas the simultaneous mutation of Y175, Y195 and Y235 results in loss of binding of downstream adapters Gads and Grb-2 (Lin and Weiss, 2001; Samelson et al, 1999; Zhang et al, 2000). Studies of LAT "knock in" mutant mice presenting the mutation of the four distal tyrosine residues of LAT in phenylalanine, called 4YF mice, showed that the murine T cell development was completely blocked (Sommers et al, 2001). Hence, their thymocyte development was arrested at the immature CD4⁻ CD8⁻ stage and no mature T cells were present.

The present invention now provides genetic evidence that LAT exerts an unanticipated and surprising inhibitory function on the differentiation of CD4 helper T ($T_H$) cells into $T_H2$ cells.

Mice homozygous for the mutation of a single LAT tyrosine (LAT Y136F) results in mice that show a precocious and spontaneous accumulation of polyclonal $T_H2$ cells, which chronically produce large amounts of interleukins 4, 5, 10 and 13. This exaggerated $T_H2$ differentiation leads in turn to tissue eosinophilia and to the maturation of massive numbers of plasma cells secreting IgE and IgG1 antibodies (see FIG. 1). Thus, in addition to known positive signaling, LAT also appears essential for establishing inhibitory signals that control T cell homeostasis.

Mice for the composite mutation of the three distal LAT tyrosines (LAT Y175F+Y195F+Y235F) prevents the development of T cells expressing alpha/beta T cell receptor. However, it allows the development of T cells expressing gamma/delta T cell receptors, and their accumulation in the periphery (see FIG. 9). These polyclonal gamma/delta T cells chronically produce large amounts of interleukins 4, 5, 10 and 13 (i.e. they present blatant TH2 phenotype). This exaggerated $T_H2$-type differentiation of gamma/delta T cells leads in turn to the maturation of massive numbers of plasma cells secreting IgE and IgG1 antibodies (see FIGS. 10 and 11).

DESCRIPTION

Figure 1:
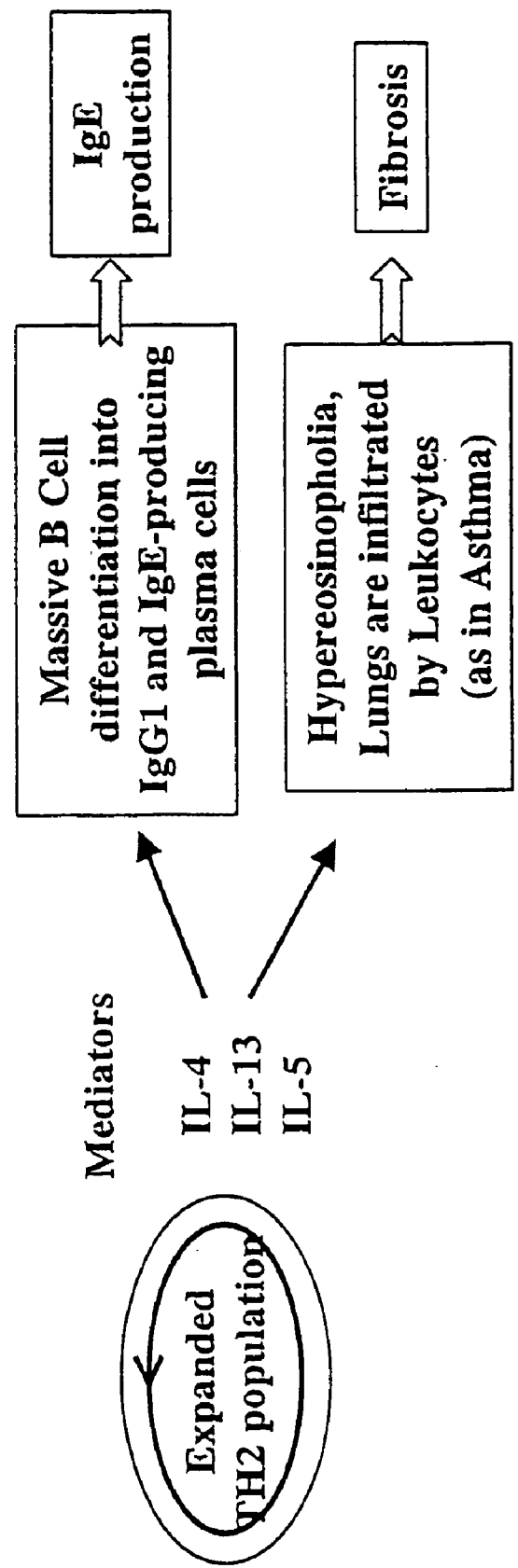
FIG. 1 is a diagram disclosing the immune system development of mutant mice.
Figure 2:
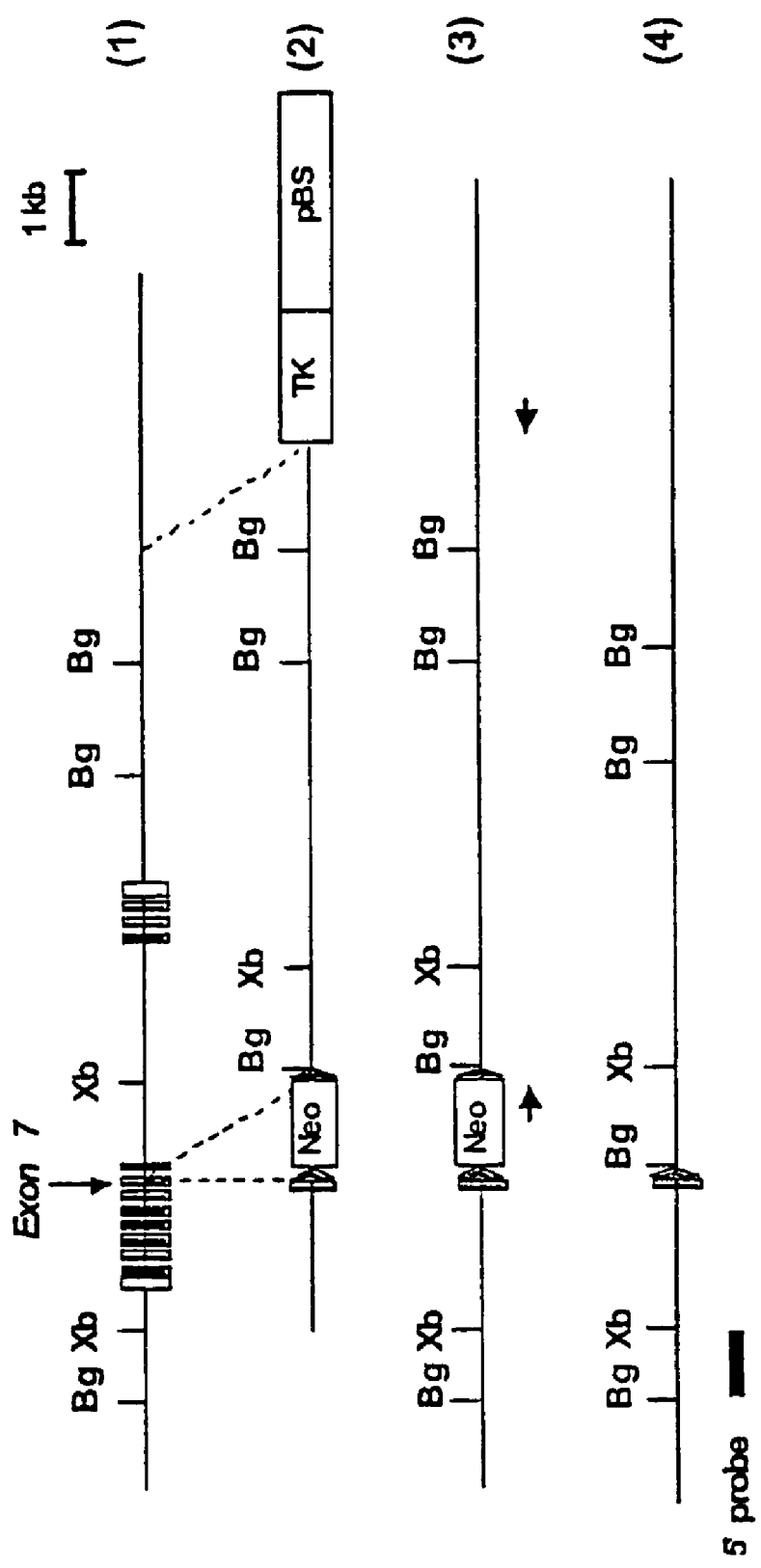
FIG. 2 illustrates the LAT Y136F knock-in strategy:
(1): the partial restriction map of the wild-type LAT gene.
(2): the targeting vector used for the introduction of the LAT Y136F mutation.
(3): the structure of the targeted allele following homologous recombination.
(4): the final structure of the targeted allele after removal of the neo$^r$ gene via Cre-mediated recombination.
Figure 3:
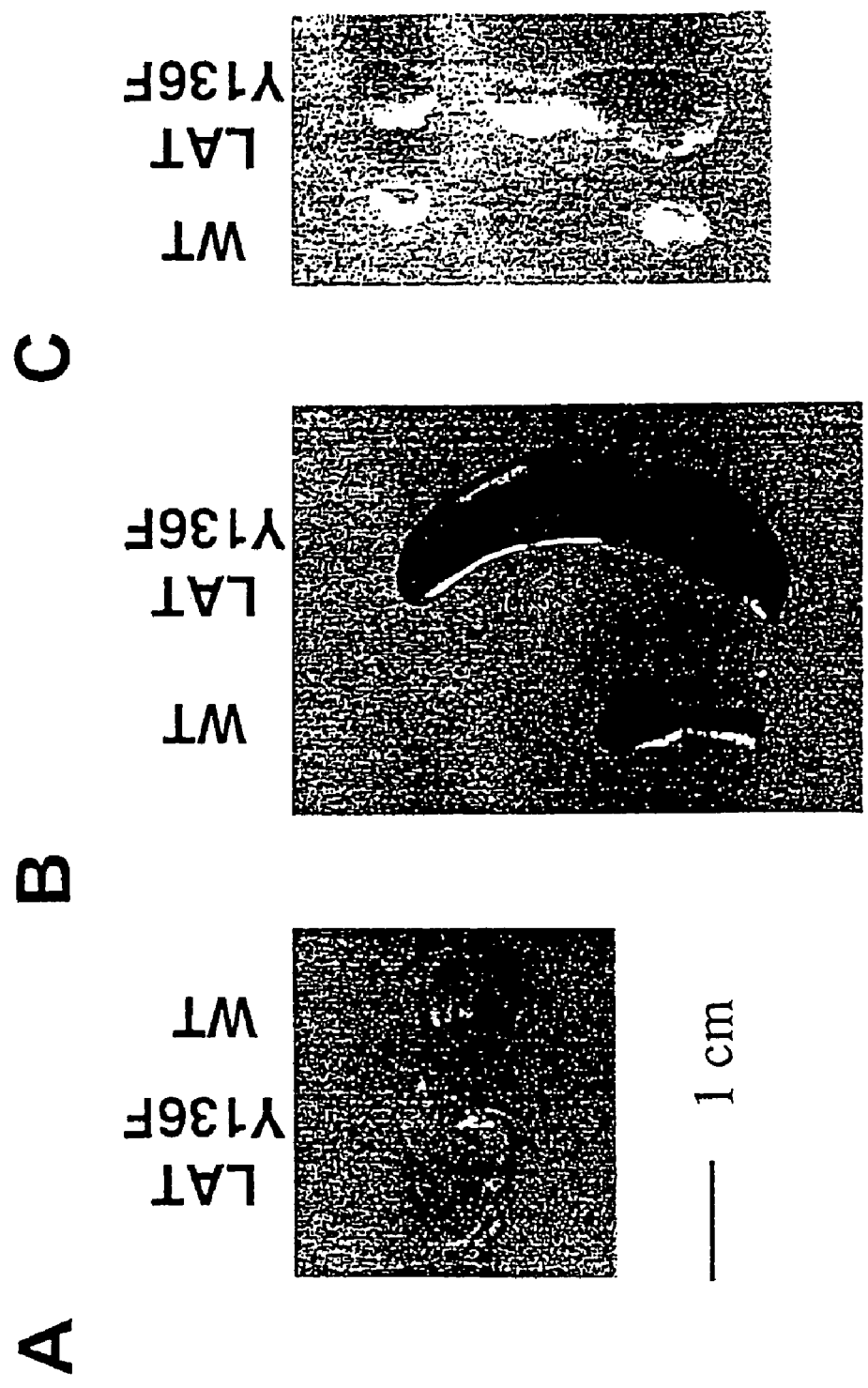
FIG. 3 illustrates the aberrant growth of lymphoid organs in the mice: thymus (A), spleen (B) and lymph nodes (C).
Figure 4:
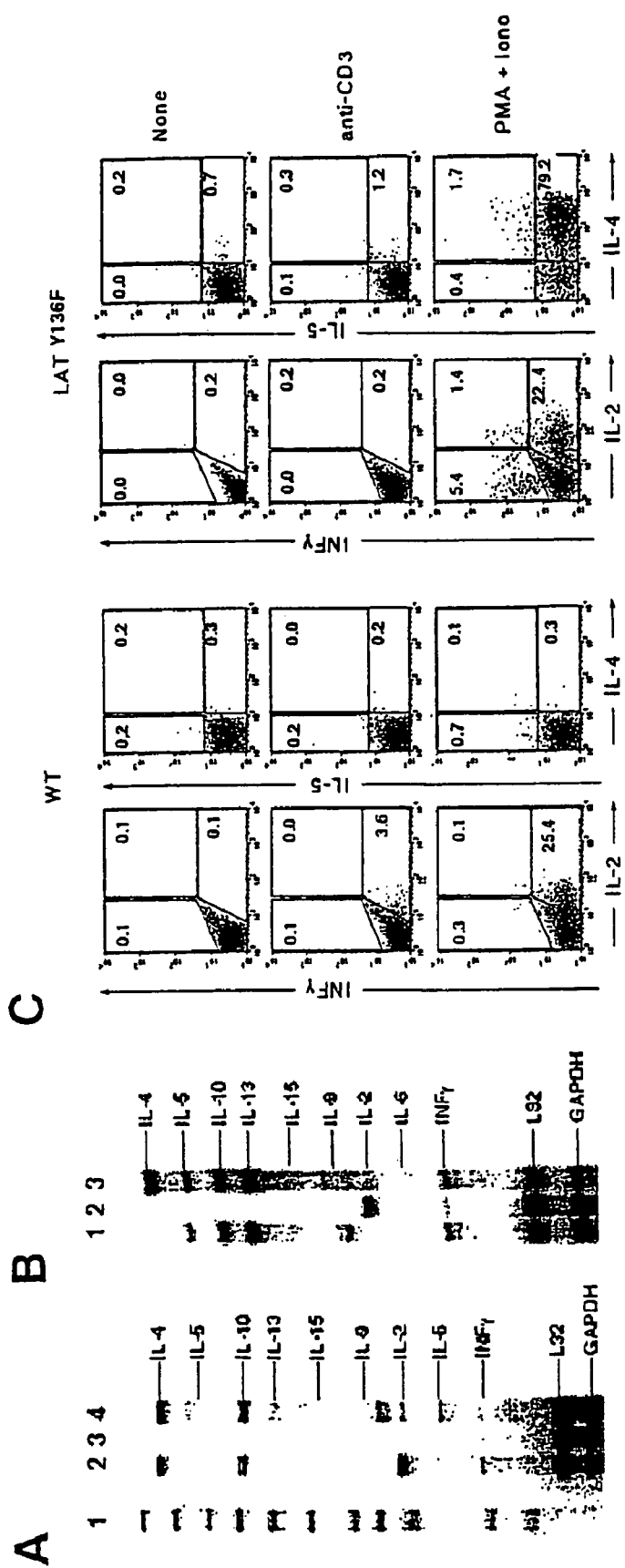
FIG. 4 relates to constitutive type-2 cytokine production in CD4 T cells freshly isolated from $LAT^{Y136F}$ peripheral lymphoid organs.
Figure 5:
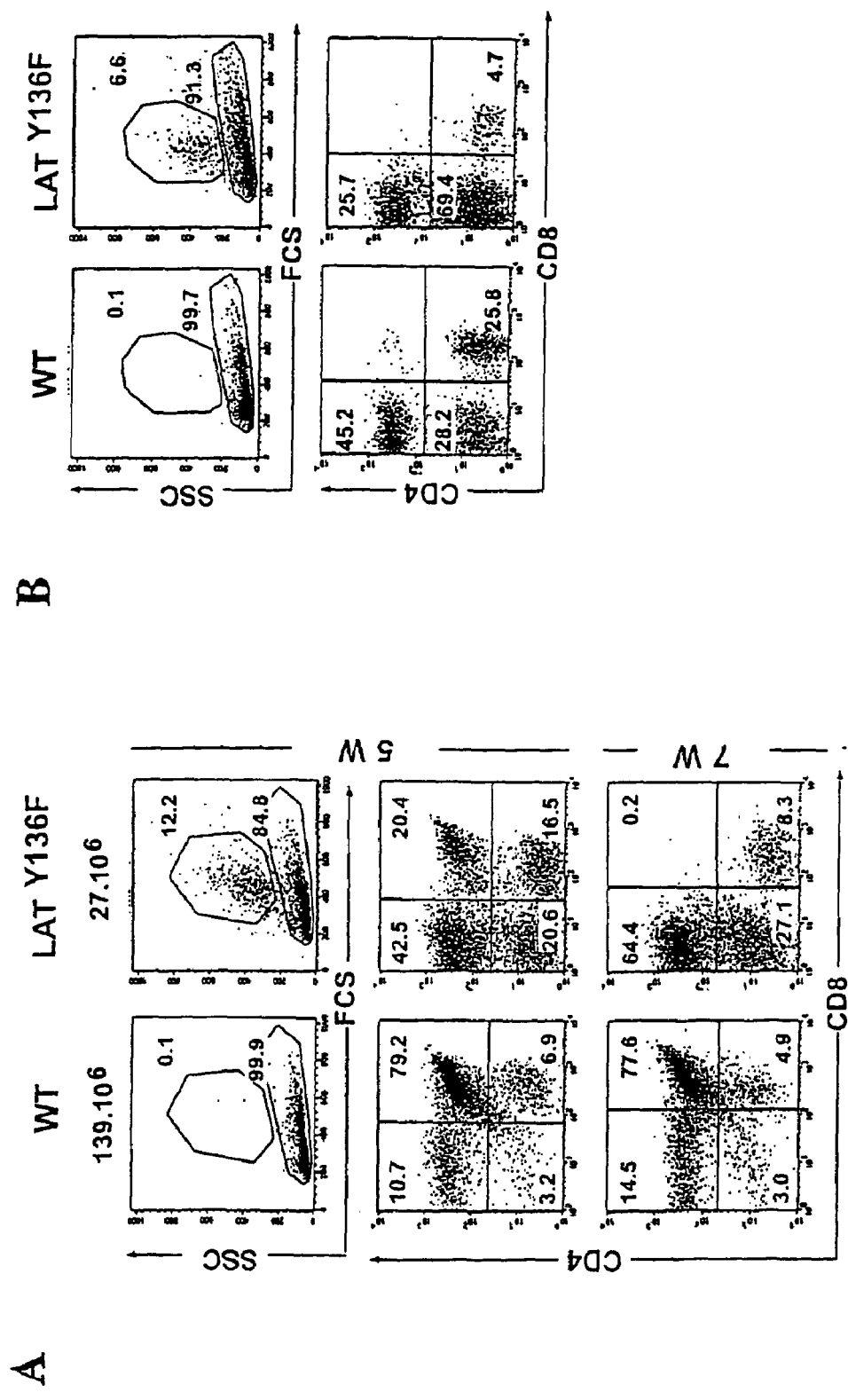
FIG. 5 relates to a phenotypic analysis of T cells from wild-type and $LAT^{Y136F}$ mice.

In this application, LAT Y136F, LAT Y175F, LAT Y195F, and $LAT^{Y235F}$ refer to the designated mutation itself, while $LAT^{Y136F}$, $LAT^{Y175F}$, $LAT^{Y195F}$ and $LAT^{Y235F}$ refer to mutants, mice or products derived from these mutations.

Mutation of one or three tyrosine(s) among the four distal tyrosine of LAT protein (i.e. LAT Y136F, or LAT Y175F+Y195F+Y235F) is able to induce the development of pathologies associated with exacerbated $T_H2$ immunity. Characteristics of the phenotype associated with this mutation are described in the following examples. Therefore, the present invention provides models of allergy and/or asthma or other diseases associated with $T_H2$ cell deregulation or activity, more particularly $T_H2$ cell accumulation. Among the advantages of said models, it is found the rapidity of the model preparation (about 3-4 weeks for a mice model instead of several months) and the exacerbated phenotype (for instance, exacerbated IgE production and tissue eosinophilia).

This phenotype due to the mutation of one or three tyrosine(s) among the four distal tyrosine residues of LAT protein (namely, LAT Y136F, or LAT Y175F+Y195F+Y235F) in mice was unpredictable, considering the phenotype of mice in which the four mutations are combined (LAT 4YF mice). Indeed, LAT 4YF mice are totally devoid of thymocytes and T cells, because of the early differentiation blockage. Therefore, the LAT 4YF mice are unable to lead or suggest the phenotype observed for the $LAT^{Y136F}$, and $LAT^{Y175F+Y195F+Y235F}$ mice. Moreover, none of the results of the previous studies on cell lines suggests such a phenotype. Furthermore, the phenotype obtained in mice with the mutation Y136F could not be extrapolated in order to deduce the expected phenotype of mice having a composite mutation Y175F+Y195F+Y235F because of the different effects of the mutation Y136F and the mutations Y175F, Y195F, and Y235F observed during the cell line studies.

The object of the present invention is to provide non-human animals having a mutated LAT gene of the invention leading to an exaggerated $T_H2$ cell differentiation. By "gene" is intended cDNA or genomic sequence coding for a LAT protein. By "mutated LAT gene of the invention" is intended a LAT gene coding for a mutant LAT protein, the sequence of which corresponds to a wild type sequence and contains the mutation of a single tyrosine among the four distal ones corresponding to Y136 in the mouse LAT protein or the composite mutation of the three distal tyrosine residues (corresponding to Y175, Y195 and Y235 in the mouse LAT protein). For example, the tyrosine corresponding to Y136 in the mouse LAT protein is the residue Y132 in the human LAT protein. In a first preferred embodiment, said LAT gene coding for a mutant LAT protein contains a single mutation of the tyrosine residue corresponding to Y136 in the mouse LAT protein. In a second preferred embodiment, said LAT gene coding for a mutant LAT protein contains the composite mutation of the three distal tyrosines, those corresponding to Y175, Y195 and Y235 in the mouse LAT protein. Preferably, said non-human animals are mice and said non-human animals have the mutated gene coding for a mutant LAT protein, the sequence of which corresponds to a wild type sequence and contains the single mutation of the tyrosine residue at position 136 or the composite mutation of the three distal tyrosine residues at positions 175, 195 and 235. Preferably, said mutation consists in the replacement by a residue preventing the association of the "tyrosine-based" sequences with the SH2 domain of proteins. More preferably, said mutation consists in the replacement of the tyrosine by a phenylalanine (Y—F), an aspartic acid (Y-D) or a glutamic acid (Y-E). Still more preferably, said mutation consists in the replacement of the tyrosine by a phenylalanine (Y—F). Preferably, said non-human animals according to the invention are mammals, and in particular, they are rodents. More preferably, said rodents are mice. Preferably, said animals are homozygous for the mutated LAT gene or are carrying a null allele of the LAT gene. Preferably, said mutated LAT gene is incorporated into the animal genome by targeted insertion in order to keep said mutated LAT gene under the control of regulatory regions of the endogenous LAT gene.

By "distal" is intended the C-terminal end of the protein. Therefore, the distal tyrosine residues are the tyrosines residues located at the C-terminal end of the protein.

In particular, the invention concerns any germ cell and somatic cell from said animals or any progeny thereof containing the mutated LAT gene of the invention. More particularly, germ cells and somatic cells of said animals contain the mutated LAT gene of the invention as a result of chromosomal incorporation into the animal genome, or into an ancestor of said animal. Preferably, said mutated LAT gene is incorporated into the animal genome by targeted insertion (homologous recombination) in order to keep said mutated LAT gene under the control of regulatory regions of the endogenous LAT gene.

Therefore, a further object of the invention is to provide a mutated mouse gene coding for a mutant LAT protein, the sequence of which corresponds to a wild type sequence and contains the single mutation of the tyrosine Y136, or a composite mutation of the tyrosine residues at positions 175, 195, and 235. Said mutation consists in the replacement by a residue preventing the association of the "tyrosine-based" sequences with the SH2 domain of proteins. Preferably, said mutation of the tyrosine leads to its replacement by a phenylalanine, an aspartic acid or a glutamic acid. More preferably, said mutation of the tyrosine leads to its replacement by a phenylalanine. In a preferred embodiment, the sequence of the gene encoding mutated mouse $LAT^{Y136F}$ protein corresponds to sequence ID No 1. The invention further includes chromosomal DNAs containing exon 7 of the mutated gene (SEQ ID No 2). The invention concerns a mouse containing said mutated mouse gene.

The present invention also encompasses plasmids comprising a DNA or a part thereof, having a sequence corresponding to the mutated gene according to the invention. In a preferred embodiment, the plasmids of the invention contain a restriction enzyme cleavage site, which is introduced in the intron 3' of exon 7. Advantageously, the restriction enzyme cleavage site is a Bgl II restriction site.

Said plasmids are useful for the generation of non-human animals according to the present invention.

Consequently, the invention also encompasses non-human embryos introduced with the plasmids of the invention, and non-human embryos obtained by homologous recombination using the plasmids of the invention. In a preferred embodiment, the non-human embryos are embryonic stem cells derived from a mouse. Advantageously, the ES cells are CK35 129/SV ES cells.

The invention also concerns the LAT mutant murine protein sequence containing the single mutation of the tyrosine Y136 or a composite mutation of the tyrosine residues at positions 175, 195, and 235. Said mutation consists in the replacement by a residue preventing the association of the "tyrosine-based" sequences with the SH2 domain of proteins. Preferably, said mutation of the tyrosine leads to its replacement by a phenylalanine, an aspartic acid or a glutamic acid. More preferably, said mutation of the tyrosine leads to its replacement by a phenylalanine. In one embodiment, the invention concerns a mutated LAT protein containing the mutated amino acid sequence of exon 7 (SEQ ID No 3).

The magnified and accelerated sequence of pathological events observed in the $LAT^{Y136F}$, and $LAT^{Y175F+Y195F+Y235F}$ mice permits to readily start tests and studies. For example, mutant $LAT^{Y136F}$ mice phenotype is achieved when they are 4 weeks old.

The mutant non-human animal according to the invention are useful in various applications of interest, in particular:
- to analyze the impact of drugs on the molecular mechanisms that lead to exacerbated IgE production as well as tissue eosinophilia, and
- as a bioreactor allowing the dedicated production of IgE antibody of known specificity prior to or following a step of humanization of the mutated LAT mouse (preferably $LAT^{Y136F}$ or $LAT^{Y175F+Y195F+235F}$ mouse).

Consequently, the present invention provides models of allergy, and/or asthma disease comprising animals according to the invention. In particular, the animals of the invention can be used as models of eosinophilia and/or $T_H2$ cells deregulation, more particularly $T_H2$ cells accumulation.

Therefore, the invention concerns the use of a mutant non-human animal according to the present invention as a model of allergy and/or asthma disease. The invention also concerns the use of a mutant non-human animal according to the present invention as a model of eosinophilia. More generally, the invention concerns the use of a mutant non-human animal according to the present invention as a model of $T_H2$ cells deregulation, more particularly a model of $T_H2$ cells accumulation.

Due to the increased sensitivity of population, health difficulties such as asthma or allergies are more frequent. The animals according to the invention are suitable models to help the research in these domains.

Accordingly, the present invention provides a method of screening for a drug for treatment of allergy, asthma and/or disease associated with $T_H2$ cell deregulation or activity comprising the step of subjecting the animals according to the invention, which are administered with the drug to a comparison with said animals, not administered with the drug.

More particularly, the invention concerns a method of screening of drugs for treatment of allergy, asthma and/or disease associated with $T_H2$ cell deregulation or activity comprising the step of:
1) administering a candidate drug to a non-human animal having a LAT gene coding for a mutant LAT protein according to the present invention;
2) evaluating the effect of said drug on the symptom or sign of allergy, asthma and/or disease associated with $T_H2$ cell deregulation or activity; and
3) selecting the drug that reduces said symptom or sign.

In a preferred embodiment, said screening method uses non-human animals not administered with drugs as control experiments. In an other preferred embodiment, said effect of said drug can be evaluated by measuring at least one parameter selected from the group: IgE level, IgG1 level, interleukin level (preferably IL-4, IL-10, IL-5 and/or IL-13), and eosinophilia. More preferably, said effect of said drug is evaluated by measuring the serum level of IgE and/or IgG1.

The invention also contemplates a method of screening drugs for treatment of allergy, asthma and/or disease associated with $T_H2$ cell deregulation or activity comprising the step of:
1) subjecting cells having a LAT gene coding for a mutant LAT protein according to the present invention to a candidate drug;
2) evaluating the effect of said drug on said cells;
3) selecting the drug having the desired effect.

In a preferred embodiment, said effect of said drug can be evaluated by measuring the interleukin production, more particularly the IL-4 production.

An other object of this invention resides in a method of screening drugs that regulate the activity of $T_H2$ cells, comprising the step of:
1) administering a candidate drug to a non-human animal having a LAT gene coding for a mutant LAT protein according to the present invention; and
2) selecting a drug that modulates the activity of $T_H2$ cells in said non-human animal.

The screening methods can be used to select, identify, characterize and/or optimize candidate drugs. The candidate drugs may be of any origin, nature and structure. Their concentration may be adjusted by the skilled artisan. Furthermore, several drugs may be tested in parallel, or in combination.

A further object of this invention is a method of producing a pharmaceutical composition for treating a disease associated with deregulated $T_H2$ cells activity, particularly asthma or allergy, the method comprising (i) selecting, identifying, optimizing or characterizing a compound using a screening assay as described above and (ii) conditioning said compound, or a derivative thereof, in a pharmaceutically acceptable carrier or vehicle.

In still another application, the present invention provides bioreactors for a large-scale production of human IgE antibodies comprising the animals according to the invention. $LAT^{Y136F}$ and $LAT^{Y175F+Y195F+Y235F}$ mice are indeed able to produce tremendous amount of IgE, as it is described in example 2. IgE produced by mutant mice are useful for applications such as desensitization or for kit of clinical assay.

Therefore, the invention concerns a method of production of human IgE antibodies comprising the steps of:
1) providing a non-human animal expressing humanized IgE;
2) breeding said animal expressing humanized IgE with a non-human animal having a LAT gene coding for a mutant LAT protein according to the present invention;
3) immunizing the animal of the progeny with an allergen;
4) recovering humanized IgE specific to said allergen. The step 4 can comprise the step of producing B cell hybridomas producing said humanized IgE specific to said allergen. The invention relates to said B cell hybridoma producing said humanized IgE specific to said allergen.

Said non-human animal expressing humanized IgE can be obtained by conventional knock-in in which the genetic segment corresponding to the constant exons of the IgE gene is substituted by the corresponding human sequence.

The invention concerns the non-human animal resulting from the breeding of the animal expressing humanized IgE with the non-human animal having a LAT gene coding for a mutant LAT protein according to the present invention.

The produced humanized IgE specific to said allergen can be used for desensitization and in clinical assays aiming at characterizing allergens, preferably atopic allergens, present in patient.

The invention contemplates the oligonucleotide probes specific to a mutated LAT gene coding for a mutant LAT protein containing the single mutation of the tyrosine corresponding to Y136 in the mouse LAT protein or a composite mutation of the three distal tyrosines (corresponding to Y175, Y195 and Y235 in the mouse LAT protein). Such probes are useful to detect the presence of the mutation in a LAT gene. Hence, the invention provide oligonucleotides, the sequence of which corresponds to SEQ ID No 4 and/or SEQ ID No 5 as probes to screen the presence of the mutation Y136 in the mouse LAT gene. More particularly, the invention concerns oligonucleotide probes specific to a mutated human LAT gene coding for a mutant LAT protein containing a single mutation of the tyrosine Y132 or a composite mutation of the tyrosine residues Y171, Y191 and Y226. Such probes are useful for the detection of mutant LAT gene involved in asthma, allergy, eosinophlia and/or any disease associated with a $T_H2$ cells deregulation or activity. Said probes can be part of a diagnostic kit.

Therefore, the invention relates to a diagnostic method for asthma, allergy, eosinophilia and/or $T_H2$ cells deregulation, more particularly $T_H2$ cells accumulation, comprising the detection of a mutated LAT gene coding for a mutant LAT protein containing a single mutation of Y132 or a composite mutation Y171+Y191+Y226. Additionally, the invention concerns a diagnostic kit for asthma, allergy, eosinophilia and/or $T_H2$ cells deregulation, more particularly $T_H2$ cells accumulation, comprising oligonucleotide probes for the detection of a mutated LAT gene coding for a mutant LAT protein containing a single mutation of Y132 or a composite mutation Y171+Y191+Y226.

Other characteristics and advantages of the invention are given in the following examples with reference to FIGS. 1 to 11.

EXAMPLES

Mutation $LAT^{Y136}$

Example 1

Production of Mutant Mice

To test in vivo the importance of $LAT^{Y136}$, the inventors generated knock-in mice with a mutation replacing Y136 with phenylalanine (Y136F).

1. Materials and Methods

Mice

Mice were maintained in a specific pathogen-free animal facility.

$LAT^{Y136F}$ Mutation.

LAT genomic clones were isolated from a 129/Ola phage library. After establishing the nucleotide sequence and the exon-intron structure of the LAT gene, the tyrosine residue found at position 136 and encoded by exon 7 was mutated to phenylalanine. Mutagenesis was performed on a 1717-bp Eco RI-Xba I fragment encompassing part of exon 5, exons 6, 7 and 8. In addition to the intended mutation, a new Bgl II restriction enzyme cleavage site was introduced in the intron 3' of exon 7 to accommodate the LoxP-flanked $neo^r$ gene and facilitate subsequent identification of $LAT^{Y136F}$ mutant mice. Finally, the targeting construct was extended to give 1.7 kb and 4.8 B kb of homologous sequences 5' and 3' of the EcoRI-XbaI fragment, respectively (see FIG. 2). After electroporation of CK35 129/SV ES cells (C. Kress et al., 1998), and selection in G418, colonies were screened for homologous recombination by Southern blot analysis. The 5' single-copy probe is a 0.9-kb Bgl II-Xba I fragment isolated from a LAT genomic clone. When tested on Bgl II-digested DNA, the 5' probe hybridizes either to a 8.5 kb wild-type fragment or to a 4.5 kb recombinant fragment. Homologous recombination events at the 3' side were screened by long range PCR. Homologous recombinant ES clones were further checked for the presence of the intended mutation by sequencing the genomic segment corresponding to exon 7. Finally, a neo probe was used to ensure that adventitious non homologous recombination events had not occurred in the selected clones.

Production of Mutant Mice.

Mutant ES cells were injected into Balb/c blastocysts. Two $LAT^{Y136F}$ recombinant ES cell clones were found capable of germ line transmission. The two mutant mouse lines were first bred to Deleter mice (Schwenk. F et al., 1995) to eliminate the Lox P-flanked neomycin cassette, and intercrossed to produce homozygous mutant mice. The two independently-derived mutant lines showed indistin-guishable phenotype. To confirm that the LAT Y136F mutation had been genuinely introduced, LAT transcripts were cloned by reverse transcription and PCR amplification from the thymus of the mutated mice, and the presence of the intended mutation confirmed by DNA sequence analysis. Screening of mice for the presence of the LAT Y136F mutation was performed by PCR using the following pairs of oligonucleotides:

```
                                        (SEQ ID N°4)
    c: 5'-GTGGCAAGCTACGAGAACCAGGGT-3';

(SEQ ID N°5)
    d: 5'-GACGAAGGAGCAAAGGTGGAAGGA-3'.
```

The single Lox P site remaining in the LAT Y136F allele after deletion of the $neo^r$ resulted in an amplified PCR product 140 bp-longer than the 510 bp-long fragment amplified from the wild-type LAT allele.

2) Mutant Mice Development

Mice homozygous for the $LAT^{Y136F}$ mutation, hereafter denoted $LAT^{Y136F}$, were born at expected Mendelian frequencies and their T cells contained levels of LAT proteins similar to wild-type T cells. At birth $LAT^{Y136F}$ mice displayed peripheral lymphoid organs of normal size. Beginning at about 3 weeks, however, the spleen and lymph nodes of the mutant mice started to enlarge relative to wild-type littermates, such that by 15 weeks of age, spleen cellularity was approximately 10 times that of wild-type mice (FIG. 3A-C). Despite marked lymphocytic infiltrations in the lung, liver and kidney, homozygotes lived to at least 17 weeks of age, and no chronic intestinal inflammation or tumor formation was observed. The effects of the LATY136F mutation were only detectable after breeding mice to homozygosity or to mice carrying a null allele of the LAT gene.

Example 2

Effect of the Mutation: Spontaneous Exaggerated T Helper Type 2 Immunity in Mice 1. Materials and Methods Purification of CD4+ T Cells and Eosinophils.

Lymph node and spleen cells from several mice were pooled and the CD4+ cells purified using a high gradient magnetic cell separation system (S. Miltenyi et al., 1990). Eosinophils were sorted on a FACSvantage™ on the basis of their FSChigh, HSA+, and CD11b+ phenotype.

Antibodies and Flow Cytometric Analysis.

Before staining, cells were preincubated on ice for at least 10 min with polyclonal mouse and rat Ig to block Fc receptors. Flow cytometric analysis was performed as described previously (M. Malissen et al., 1995). All the antibodies were from BD PharMingen except the anti-CCR3 antibody that was purchased from R&D.

Staining for Intracellular Cytokines.

Before intracellular cytokine staining, cells ($1.5 \times 10^6$) were cultured for 4 h in the presence of monensin (GolgiStop; BD PharMingen) at a final concentration of 2 µM. Cells were then immediately placed on ice, washed, resuspended in PBS 1×, 1% FCS, 0.20% sodium azide, and stained with an APC-conjugated anti-CD4 antibody. For intracellular cytokine staining, cells were first fixed using the cytofix/cytoperm kit (BD PharMingen). Each cell sample was subsequently split into aliquots that were separately stained with (1) a combination of FITC-conjugated anti-IFN-α and PE-conjugated anti-IL-2 antibodies, (2) a combination of FITC-conjugated anti-IL-5 and PE-conjugated anti-IL-4 antibodies, and (3) a combination of fluorochrome-conjugated and isotype-matched negative control Ig (BD PharMingen). After a final wash, CD4+ cells ($10^4$) were analyzed on a FACSCalibur™ flow cytometer after gating out dead cells using forward and side scatters.

RNase Protection Assay.

For multiplex cytokine transcript analysis, total cellular RNA was isolated from the specified cells using TRIzol (GIBCO-BRL Life Technologies) and analyzed by ribonuclease protection assay using an MCK-1 RiboQuant™ custom mouse template set (BD Pharmingen). Briefly, $^{32}$P-labeled riboprobes were mixed with 10 μg of RNA, incubated at 56° C. for 12 to 16 hours, and then treated with a mixture of RNases A and T1 and proteinase K. RNase-protected $^{32}$P-labeled RNA fragments were separated on denaturing polyacrylamide gels and the intensity of the bands evaluated with a Fuji imaging plate system.

Determination of Serum Isotype-specific Immunoglobulin Levels.

The titres of polyclonal IgM, IgG1, IgG2a, IgG2b, IgG3 and IgA antibodies and κ and λ light chains were determined using isotype-specific ELISA (Southern Biotechnology). The concentrations of IgG1 and IgE were determined by comparing test sample dilution series values with isotype control standards.

2. Results

A prominent phenotype of the CD4 T cells found in $LAT^{Y136F}$ mice was revealed when the inventors measured their ability to make cytokines. Due to the short half-lives of cytokines and of their transcripts, their analysis generally requires restimulation of T cells in vitro with PMA and ionomycin. A multiprobe RNase protection assay detecting levels of transcripts of 9 cytokines showed that CD4 T cells freshly isolated from $LAT^{Y136F}$ mice contained sufficient IL-4 and IL-10 transcripts to allow their detection even without ex vivo restimulation (FIG. 4A). Upon activation by PMA/ionomycin the levels of IL-4 and IL-10 transcripts they contained were further increased, and IL-5, IL-13, and IFN-α transcripts became readily detectable (FIG. 4B). In marked contrast, wild-type CD4 T cells yielded only the IL-2 and IFN-α transcripts expected for primary T cells. Analysis of IL-4 production at the single cell level, showed that following a 4 hr activation with PMA/ionomycin, close to 80% of the CD4 T cells isolated from $LAT^{Y136F}$ mice expressed very high levels of IL-4 (FIG. 4C). Consistent with the notion that these CD4 T cells were refractory to TCR stimuli, none of them scored as IL-4+ in response to TCR cross-linking (FIG. 4C). Thus, $LAT^{Y136F}$ spontaneously developed a high frequency of $T_H2$ cells. In the case of wild-type CD4 T cells, $T_H2$ polarization of such magnitude is only achieved following prolonged antigenic stimulation in the presence of IL-4.

Figure 6:
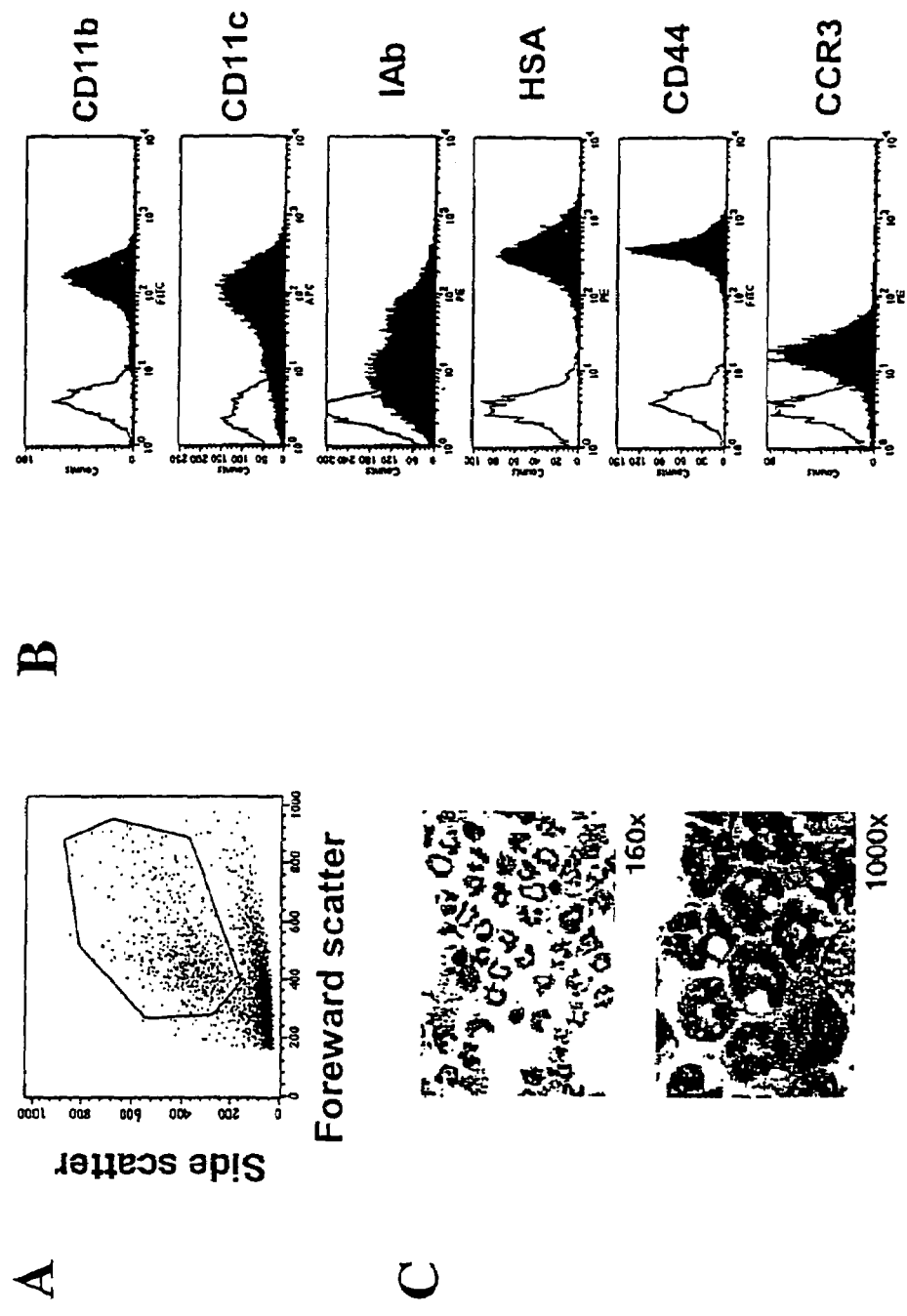
FIG. 6 illustrates eosinophilia in 6 weeks old LATY136F lymphoid organs.
A: Dot plot panel showing the gate selected for the analysis described in panel B and for the sorted cells picture in panel C.
B: Single color histograms of gated cells labelled with antibodies characterizing eosinophils.
C: Hematoxylin and eosin staining of sorted cells.
Figure 7:
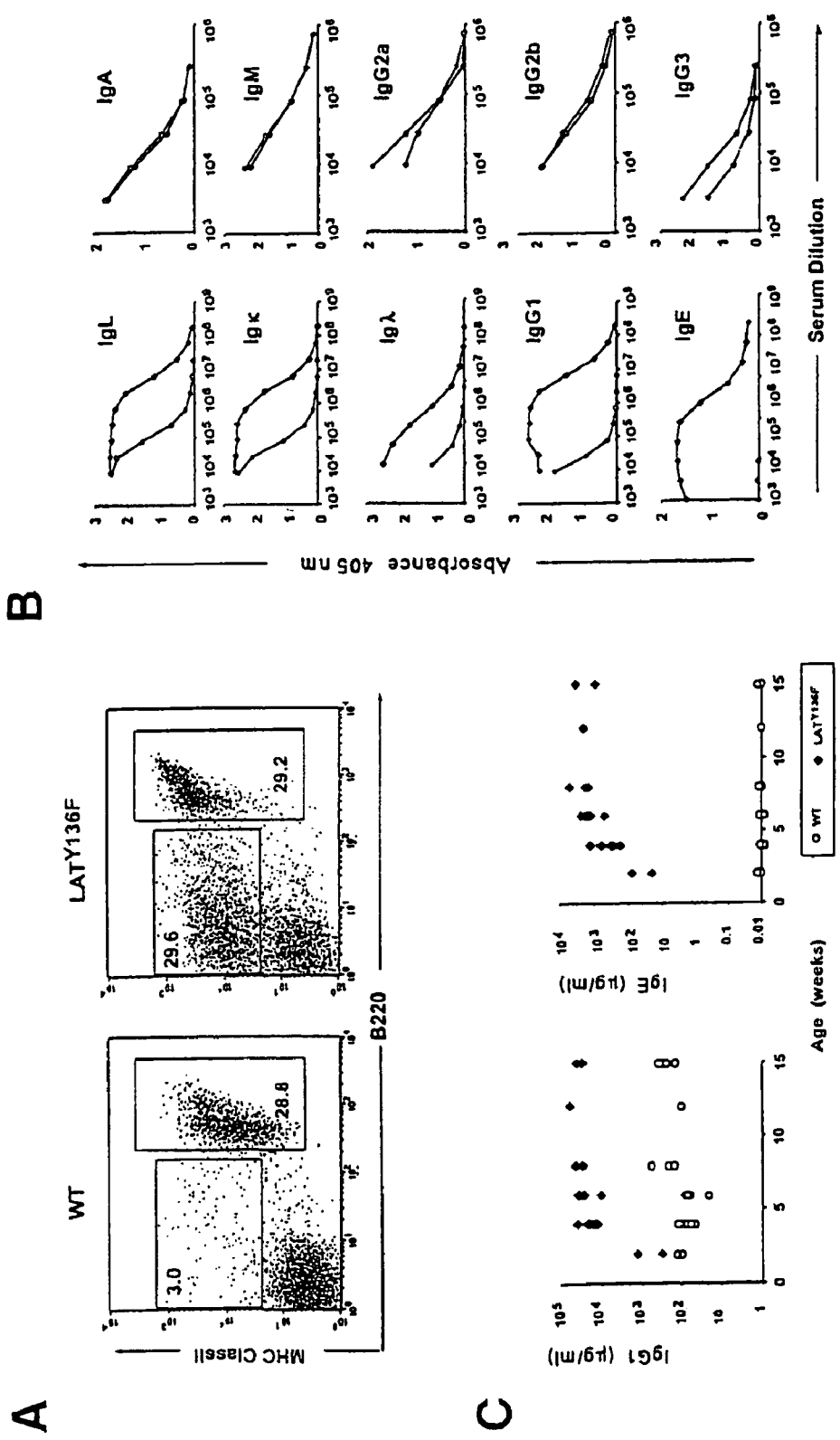
FIG. 7 illustrates the hyperactivity of B lymphocytes: massive serum levels of IgE and IgG1 antibodies in unimmunized $LAT^{Y136F}$ mice.
Figure 8:
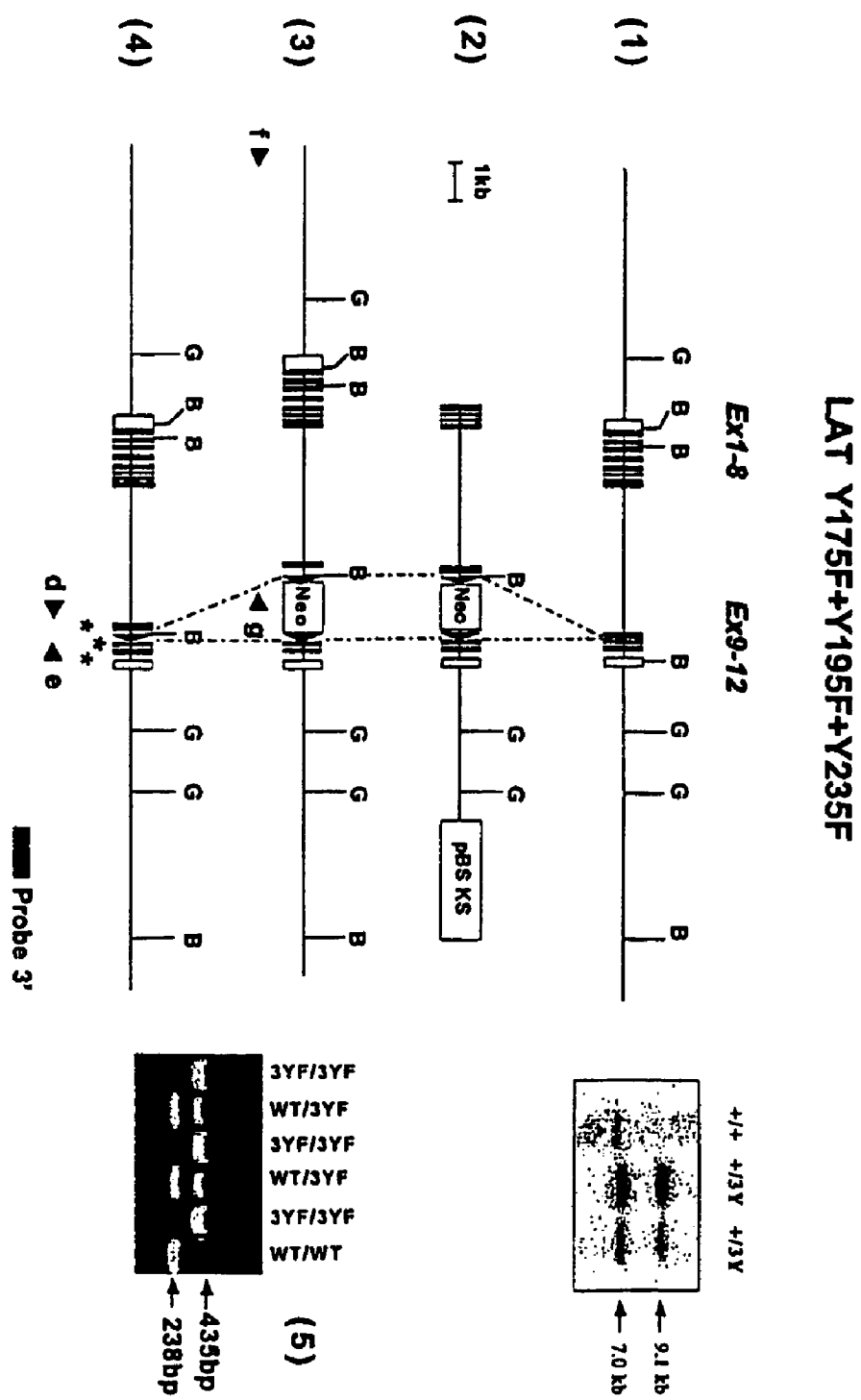
FIG. 8 illustrates the LAT Y175F+Y195F+Y235F knock in strategy:
(1): the partial restriction map of the wild-type LAT gene.
(2): the targeting vector used for the introduction of the LAT Y175F, Y195F and Y235F mutation.
(3): the structure of the targeted allele following homologous recombination.
(4): the final structure of the targeted allele after removal of the neo$^r$ gene via Cre-mediated recombination.
Figure 9:
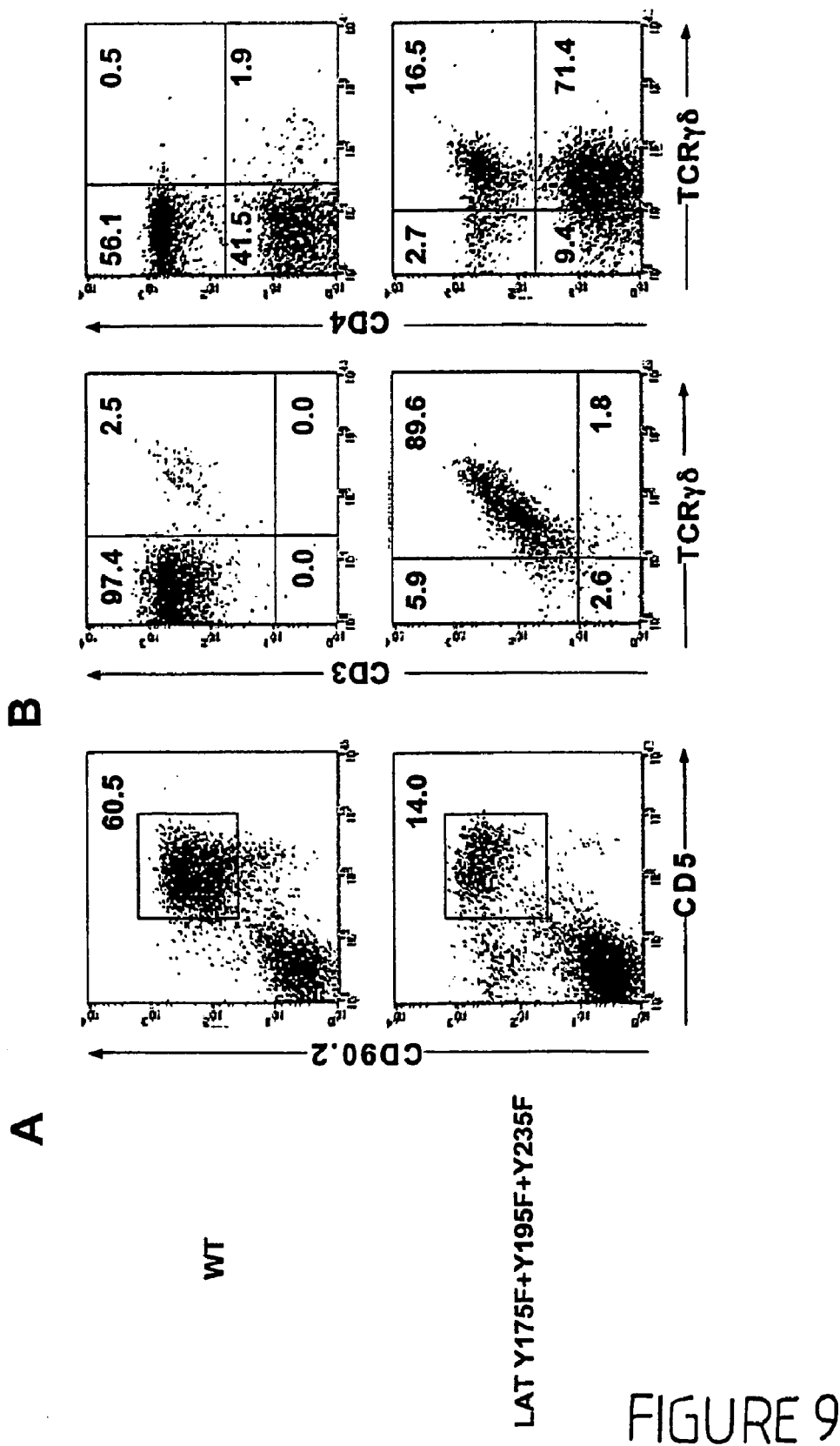
FIG. 9 relates to a phenotypic analysis of the gamma/delta T cells developed in large numbers in the LAT Y175F+ Y195F+Y235F mutant in the mere absence of alpha/beta T cells.

Light scatter analysis of thymic and lymph node cells from $LAT^{Y136F}$ mice older than 4 weeks revealed a unique cell population that was almost absent from age-matched wild-type mice, and showed both an intermediate forward scatter and a high side scatter (FIG. 5A, 5B, 6A). Based on several of criteria, these cells were identified as eosinophils (FIG. 6). Minute numbers of eosinophils normally reside in wild-type thymi, and their augmentation in $LAT^{Y136F}$ thymi may primarily result from an intrinsic expression of $LAT^{Y136F}$ molecules. However, LAT transcripts were undetectable in eosinophils purified from $LAT^{Y136F}$ mice, meaning that the thymic and lymph node eosinophilia they manifest result from the production of IL-5 by the abnormal CD4 cells present in these mutant mice.

Secondary lymphoid organs of 6-week old $LAT^{Y136F}$ mice contained 7 to 10 times more B cells than their wild-type counterparts. Thus, the splenomegaly and generalized lymphadenopathy that developed in young $LAT^{Y136F}$ mice can be mostly accounted for by cells belonging to the T and B cell lineages. Over 90% of the mature B cells found in the spleen and lymph nodes of 6-week old wild type littermates had a resting phenotype (FIG. 7A). In marked contrast, only 25% of the B cells found in the enlarged secondary lymphoid organs of age-matched $LAT^{Y136F}$ littermates showed a resting phenotype. Among the remaining B cells, 25% showed an hyper-activated phenotype, and 50% expressed a phenotype typical of antibody producing cells. Coincident with the presence of these latter cells, serum IgG1 concentrations were elevated approximately 200 times compared to wild-type mice, whereas those of IgE were elevated 2500 to 10000 times (FIG. 7C). In contrast, the levels of the other Ig isotypes did not differ significantly from those of wild-type serum (FIG. 7B). In support of a polyclonal hypergammaglobulinemia G1 and E, the concentrations of kappa and lambda light chains were both markedly augmented in the serum of $LAT^{Y136F}$ mice (FIG. 7B). Notably, IgE and IgG1 antibody concentrations reached a plateau as early as 5 weeks of age (FIG. 7C), the values of which exceeded the extraordinarily large amounts of IgE and IgG1 previously reported for mice deprived of NFATc2 and NFATc3 transcription factors. Given that B cells do not express LAT proteins, and considering that isotype switching to IgE and IgG1 is highly dependent on the presence of IL-4 and IL-13, the overproduction of IgE and IgG1 noted in $LAT^{Y136F}$ mice is secondary to the presence of an abnormally high frequency of $T_H2$ effectors.

Example 3

Production of IgE

Mice expressing humanized IgE are developed by conventional knock-in strategy in which the genetic segment corresponding to the constant exons of the IgE gene is substituted by the corresponding human sequence. Mice with a humanized IgE locus are bred into $LAT^{Y136F}$ mice. Following immunization, B cell hybridomas producing specific human IgE are produced, and the resulting specific human IgE are used as "standard" in clinical assays aiming at characterizing atopic allergens present in patients."

Example 4

Screening for a Drug

Mutant mice and control ones will be treated with a variety of drugs or original compounds. Their effects will be analyzed in vivo by measuring various parameters such as:

$T_H2$ cells differentiation.

Production of $T_H2$ types cytokines

Eosinophilia

Hypergammaglobulinemia G1 and E.

Mutation LAT$^{Y175+Y195+Y235}$

Example 5

Production of Mutant Mice

To test in vivo the importance of the three carboxy-terminal tyrosines (LAT Y175, LAT Y195 and LAT Y235), the inventors generated knock-in mice with a mutation replacing these three tyrosines with phenylalanine (LAT Y175F+Y195F+Y235F).

1. Materials and Methods

Mice

Mice were maintained in a specific pathogen-free animal facility.

LAT Y175F+Y195F+Y235F mutation.

LAT genomic clones were isolated from a 129/Ola phage library. After establishing the nucleotide sequence and the exon-intron structure of the LAT gene(EMBL Nucleotide Sequence Datatase; accession number: AJ438435), the tyrosine residues found at positions 175, 195 and 235 and encoded by exons 9, 10, 11 were mutated to phenylalanine. Mutagenesis was performed on a 815 bp NcoI-BamHI fragment encompassing exons 9, 10, 11 (coding for tyrosines 175 (exon 9), 195 (exon 10) and 235 (exon 11) and part of exon 12 (corresponding to the 3' untranslated region of LAT). Each exon was mutated independently and new restriction sites were introduced for facilitating subsequent cloning steps. A new Eco RI site was introduced on the 5' side of the NcoI site, BamHI and ClaI sites were introduced between exons 9 and 10, a HindIII site was introduced between exons 10 and 11, and BglII, XhoI, and NotI sites were introduced on the 3' side of exon 11 in lieu of the original BamHI site. PCR reactions were performed with Pwo DNA polymerase (Boehringer Mannheim), and PCR products were purified and cut with with EcoRI and BamHI for exon 9, BamHI and HindIII for exon 10, and HindIII and NotI for exon 11. These three fragments were assembled in a pBS-KS plasmid (Stratagene). The resulting plasmid was used to clone a 3.5 kb Eco RI-Nco I genomic fragment providing a 5' homology arm and a 4.3 kb-Sal I genomic fragment providing a 3' homology arm. Finally a loxP flanked neo$^r$ gene was introduced using the BamHI and ClaI sites that were engineered between exons 9 and 10. After electroporation of CK35 129/SV embryonic stem (ES) cells and selection in G418, colonies were screened for homologous recombination by southern blot analysis using a 3' single-copy probe that consisted of a 1.1 kb EcoRI-HindIII fragment isolated from a LAT genomic clone. When tested on BamHI digested genomic DNA, the 3' probe hybridizes either to a 7.0 kb wild-type fragment or to a 9.1 kb recombinant fragment. The presence of a genuine recombination event was checked by PCR using the following pair of primers (depicted in FIG. 8):

```
f: 5'-CCCAGAGGCAAACCCTCTGAAG-3'    (SEQ ID N° 6)
and g: 5'-TCGAATTCGCCAATGACAAGACGC-3'.  (SEQ ID N° 7)
```

This PCR gives a band of 8.6 kb in the recombinant ES clones only. Homologous recombinant ES clones were further checked for the presence of the intended mutations by sequencing the genomic segment corresponding to exons 9, 10 and 11. Finally, a neo probe was used to ensure that adventitious non-homologous recombination events had not occured in the selected clones.

Production of Mutant Mice.

Mutant ES cells were injected into Balb/c blastocysts. Two LAT Y175F+Y195F+Y235F recombinant ES cell clones were found capable of germ line transmission. The two mutant mouse lines were first bred to Deleter mice (Schwenk. F et al., 1995) to eliminate the Lox P-flanked neomycin cassette, and intercrossed to produce homozygous mutant mice. The two independently-derived mutant lines showed indistinguishable phenotype. To confirm that the LAT Y175F+Y195F+Y235F mutation had been genuinely introduced, LAT transcripts were cloned by reverse transcription and PCR amplification from the thymus of the mutated mice, and the presence of the intended mutation confirmed by DNA sequence analysis. Screening of mice for the presence of the LAT Y175F+Y195F+Y235F mutation was performed by PCR using the following pairs of oligonucleotides:

```
d: 5'-GGAGACTTAGATGTCTGAGCCG-3'    (SEQ ID N° 8)
and e: 5'-GACAGACCAGCAGGGACAGTG-3'     (SEQ ID N° 9)
(Wt 238 bp, mutant 435 bp).
```

The single Lox P site remaining in the LAT Y175F+Y195F+Y235F allele after deletion of the neo$^r$ resulted in an amplified PCR product 140 bp-longer than the 510 bp-long fragment amplified from the wild-type LAT allele.

2) Mutant Mice Development

Mice homozygous for the LAT Y175F+Y195F+Y235F mutation, hereafter denoted LAT Y175F+Y195F+Y235F were born at expected Mendelian frequencies and their T cells contained levels of LAT proteins similar to wild-type T cells. At birth LAT Y175F+Y195F+Y235F mice displayed peripheral lymphoid organs of normal size. Beginning at about 3 months, however, the spleen and lymph nodes of the mutant mice started to enlarge relative to wild-type littermates, such that by 3 months of age, spleen cellularity was approximately 5 times that of wild-type mice. Homozygotes lived to at least 5 months of age, and no chronic intestinal inflammation or tumor formation was observed. The effects of the LAT Y175F+Y195F+Y235F mutation were only detectable after breeding mice to homozygosity or to mice carrying a null allele of the LAT gene.

Example 6

Effect of the Mutation: a Subset of Amma/Delta T Cells Expands and Acquire a Spontaneous Exaggerated T Helper Type 2 Immunity in Mice 1. Materials and Methods Purification of Gamma/Delta T Cells and Eeosinophils.

Spleen cells from several mice were pooled and the gamma/delta T cells purified using a high gradient magnetic cell separation system (S. Miltenyi et al., 1990).

Antibodies and Flow Cytometric Analysis.

Before staining, cells were preincubated on ice for at least 10 min with polyclonal mouse and rat Ig to block Fc receptors. Flow cytometric analysis was performed as described previously (M. Malissen et al., 1995). All the antibodies were from BD PharMingen.

Staining for Intracellular Cytokines.

Before intracellular cytokine staining, cells ($1.5 \times 10^6$) were cultured for 4 h in the presence of monensin (GolgiStop; BD PharMingen) at a final concentration of 2 µM. Cells were then immediately placed on ice, washed, resuspended in PBS 1×, 1% FCS, 0.20% sodium azide, and stained with an APC-conjugated anti-CD5 antibody. For intracellular cytokine staining, cells were first fixed using the cytofix/cytoperm kit (BD PharMingen). Each cell sample was subsequently split into aliquots that were separately stained with (1) a combination of FITC-conjugated anti-IFN-☐ and PE-conjugated anti-IL-2 antibodies, (2) a combination of FITC-conjugated anti-IL-5 and PE-conjugated anti-IL-4 antibodies, and (3) a combination of fluorochrome-conjugated and isotype-matched negative control Ig (BD PharMingen). After a final wash, CD5+ cells ($10^4$) were analyzed on a FACSCalibur™ flow cytometer after gating out dead cells using forward and side scatters.

RNase Protection Assay.

For multiplex cytokine transcript analysis, total cellular RNA was isolated from the specified cells using TRIzol (GIBCO-BRL Life Technologies) and analyzed by ribonuclease protection assay using an MCK-1 RiboQuant™ custom mouse template set (BD Pharmingen). Briefly, $^{32}$P-labeled riboprobes were mixed with 10 µg of RNA, incubated at 56° C. for 12 to 16 hours, and then treated with a mixture of RNases A and T1 and proteinase K. RNase-protected $^{32}$P-labeled RNA fragments were separated on denaturing polyacrylamide gels and the intensity of the bands evaluated with a Fuji imaging plate system.

Determination of Serum Isotype-specific Immunoglobulin Levels.

The titres of polyclonal IgM, IgG1, IgG2a, IgG2b, IgG3 and IgA antibodies and ☐ and ☐ light chains were determined using isotype-specific ELISA (Southern Biotechnology). The concentrations of IgG1 and IgE were determined by comparing test sample dilution series values with isotype control standards.

2. Results

Figure 10:
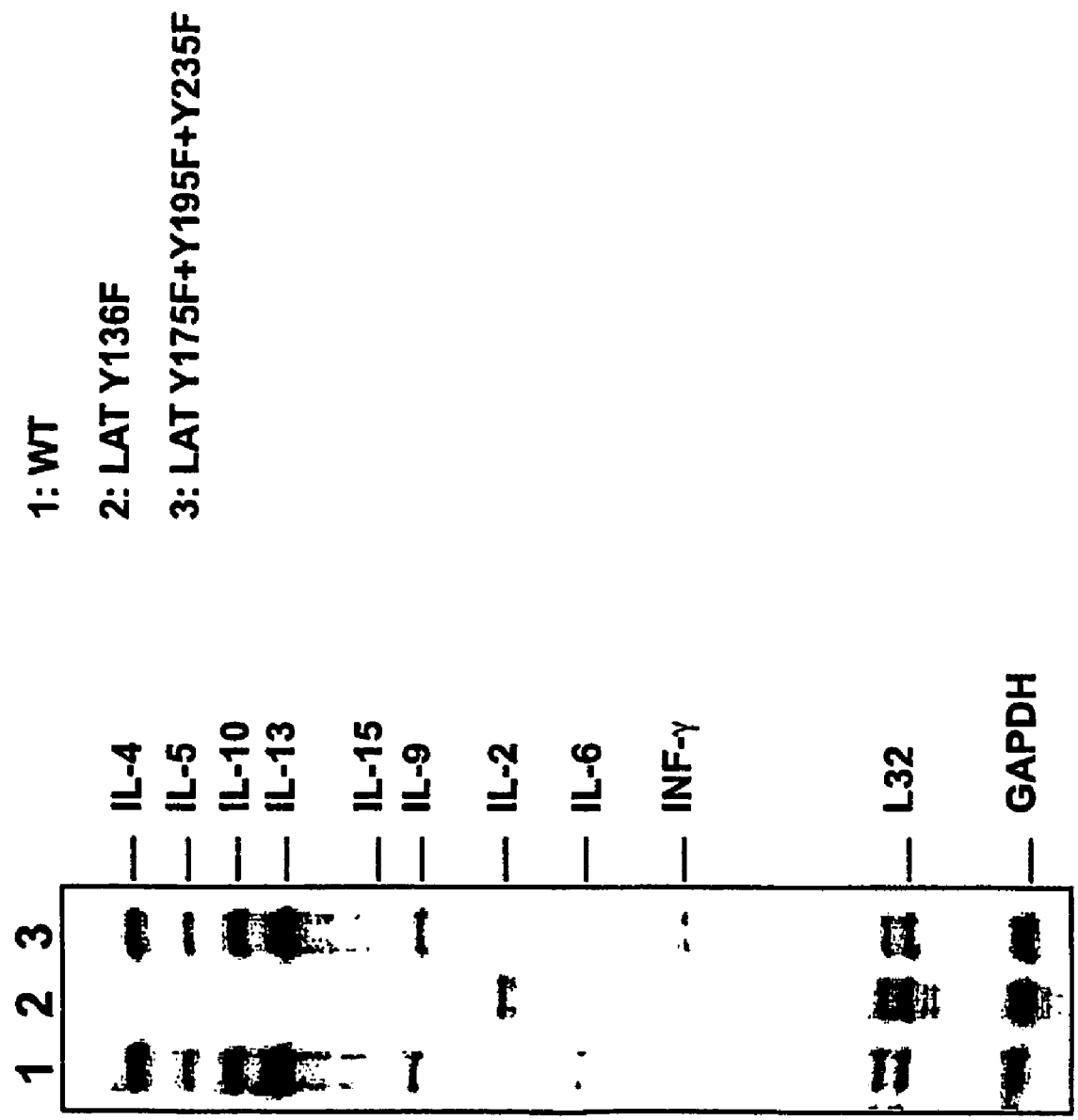
FIG. 10 illustrates the $T_H2$-type cytokines that are spontaneously produced by the gamma/delta T cells present in LAT Y175F+Y195F+Y235F mutant mice (lane 3) and compare them the $T_H2$-type cytokines that are spontaneously produced by the alpha/beta T cells developed in the $LAT^{Y136F}$ mutant (lane 1).

A prominent phenotype of the $CD90.2^+$, $CD5^+$ gamma/delta T cells found in LAT Y175F+Y195F+Y235F mice (see FIG. 9) was revealed when the inventors measured their ability to make cytokines. Due to the short half-lives of cytokines and of their transcripts, their analysis generally requires restimulation of T cells in vitro with PMA and ionomycin. A multiprobe RNase protection assay detecting levels of transcripts of 9 cytokines showed that gamma/delta T cells freshly isolated from LAT Y175F+Y195F+Y235F mice contained large amounts of IL-4, IL-5, IL-10 and IL-13 transcripts to (FIG. 10). This attribute is reminiscent of the observation made with the alpha/beta T cells present in the periphery of the LAT Y136F mice. In marked contrast, wild-type CD4 T cells yielded only the IL-2 and IFN-γ transcripts expected for primary T cells. Analysis of IL-4 production at the single cell level, showed that following a 4 hr activation with PMA/ionomycin, close to 80% of the CD4 T cells isolated from LAT Y175F+Y195F+Y235F mice expressed very high levels of IL-4. Thus, LAT Y175F+Y195F+Y235F mice spontaneously developed a high frequency of gamma/delta T cells with a Th2 phenotype. In the case of wild-type CD4 T cells, $T_H2$ polarization of such magnitude is only achieved following prolonged antigenic stimulation in the presence of IL-4.

Figure 11:
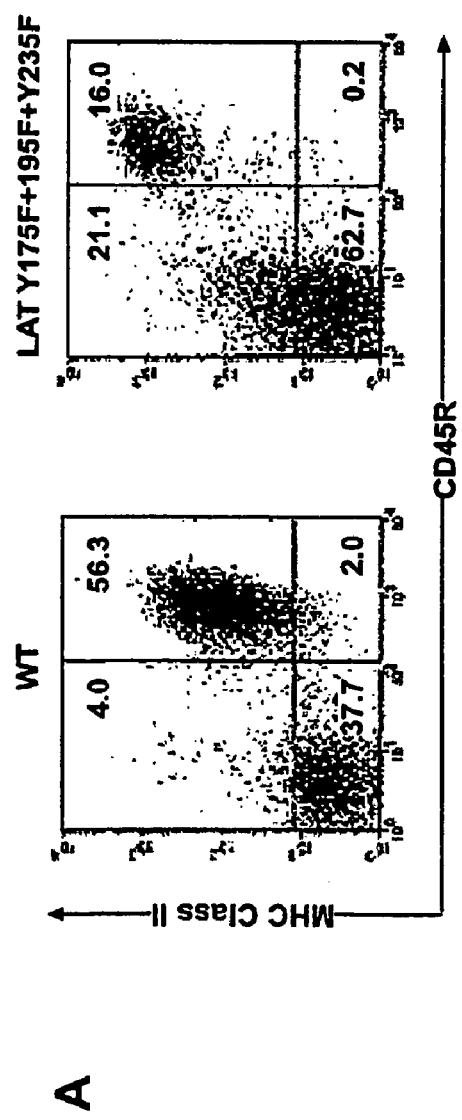
FIG. 11 illustrates the hyperactivity of B lymphocytes and the massive amounts of IgE anf IgG1 that are spontaneously found in the serum of unimmunized LAT Y175F+Y195F+ Y235F mice.
Figure 11:
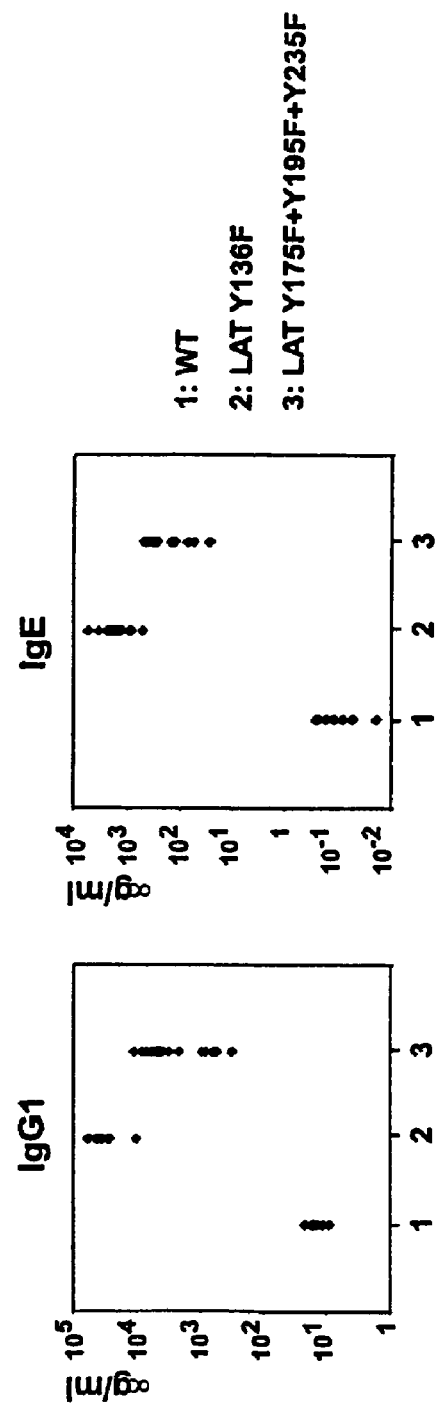

The spleen of 3-month old LAT Y175F+Y195F+Y235F mice contained 5 to 10 times more B cells than their wild-type counterparts. Thus, the splenomegaly that developed in LAT Y175F+Y195F+Y235F mice can be mostly accounted for by cells belonging to the T and B cell lineages. Over 90% of the mature B cells found in the spleen and lymph nodes of 3-month old wild type littermates had a resting phenotype (FIG. 11A). In marked contrast, only 16% of the B cells found in the enlarged secondary lymphoid organs of age-matched LAT Y175F+Y195F+Y235F littermates showed a resting phenotype. Among the remaining B cells, 21% showed an hyperactivated phenotype, and 63% expressed a phenotype typical of antibody producing cells. Coincident with the presence of these latter cells, serum IgG1 concentrations were elevated approximately 100 times compared to wild-type mice, whereas those of IgE were elevated 500 to 5000 times (FIG. 11). In contrast, the levels of the other Ig isotypes did not differ significantly from those of wild-type serum. Given that mature B cells do not express LAT proteins, and considering that isotype switching to IgE and IgG1 is highly dependent on the presence of IL-4 and IL-13, the overproduction of IgE and IgG1 noted in LAT Y175F+Y195F+Y235F mice is secondary to the presence of an abnormally high frequency of gamma/delta T cells producing $T_H2$ cytokines.

Example 7

Production of IgE

Mice expressing humanized IgE are developed by conventional knock-in strategy in which the genetic segment corresponding to the constant exons of the IgE gene is substituted by the corresponding human sequence. Mice with a humanized IgE locus are bred into LAT Y175F+Y195F+Y235F mice. Following immunization, B cell hybridomas producing specific human IgE are produced, and the resulting specific human IgE are used as "standard" in clinical assays aiming at characterizing atopic allergens present in patients."

Example 8

Screening for a Drug

Mutant mice and control ones will be treated with a variety of drugs or original compounds. Their effects will be analyzed in vivo by measuring various parameters such as:

$T_H2$ cells differentiation.

Production of $T_H2$ types cytokines

Hypergammaglobulinemia G1 and E.

REFERENCES

Kress, C., Vandormael-Pournin, S., Baldacci, P., Cohen-Tannoudji, M., and Babinet, C. (1998). Nonpermissiveness for mouse embryonic stem (ES) cell derivation circumvented by a single backcross to 129/Sv strain: establishment of ES cell lines bearing the Omd conditional lethal mutation, Mamm Genome 9, 998-1001.

Lin, J., and Weiss, A. (2001). Identification of the minimal tyrosine residues required for linker for activation of T cell function, J Biol Chem 276, 29588-29595.

Malissen, M., Gillet, A., Ardouin, L., Bouvier, G., Trucy, J., Ferrier, P., Vivier, E., and Malissen, B. (1995). Altered T cell development in mice with a targeted mutation of the CD3–epsilon gene, Embo J 14, 4641-53.

Miltenyi, S., Muller, W., Weichel, W., and Radbruch, A. (1990). High gradient magnetic cell separation with MACS, Cytometry 11, 231-8.

Samelson, L. E., Bunnell, S. C., Trible, R. P., Yamazaki, T., and Zhang, W. (1999). Studies on the adapetr molecule LAT, Cold Spring Harbor Symposia On Quantitative Biology, Biology Laboratory, Cold Spring Harbor, N.Y., No 64, 259-263.

Schwenk, F., Baron, U., and Rajewsky, K. (1995). A cre-transgenic mouse strain for the ubiquitous deletion of loxP-flanked gene segments including deletion in germ cells, Nucleic Acids Res 23, 5080-1.

Sommers, C. L., Menon, R. K., Grinberg, A., Zhang, W., Samelson, L. E., and Love, P. E. (2001). Knock-in mutation of the distal four tyrosines of linker for activation of T cells blocks murine T cell development, J Exp Med, 2001, 135-142.

Zhang, W., Trible, R. P., Zhu, M., Liu, S. K., McGlade, C. J., and Samelson, L. E. (2000). Association of Grb2, Gads, and phospholipas C-γ1 with phosphorylated LAT tyrosine residues, J Biol Chem, 275, 23355-23361.

The invention claimed is:

1. A mouse whose genome comprises a mutant LAT gene encoding a mutant mouse LAT protein, wherein the amino acid sequence of said mutant mouse LAT protein comprises a single mutation of a tyrosine located at position 136 of the wild-type mouse LAT protein sequence, wherein the mutation is not a composite mutation of the tyrosine residue at positions 175, 195 and 235 of said wild-type mouse LAT protein sequence, wherein the single mutation of the tyrosine located at position 136 consists of a replacement with a residue preventing the association with SH2 domain of proteins, wherein said mutant LAT gene replaces the endogenous wild-type LAT gene such that the mutant LAT gene is under the control of the regulatory regions of the endogenous LAT gene, and wherein the mouse is homozygous for said mutant mouse LAT gene, and wherein the mouse has a phenotype of exaggerated TH2 cell differentiation.

2. The mouse according to claim 1, wherein said mutant LAT gene encodes a mutant LAT protein comprising the mutated amino acid sequence of exon 7(SEQ ID NO:3).

3. The mouse according to claim 1, wherein said single mutation consists in the replacement of the tyrosine by a phenylalanine (Y—F), an aspartic acid (Y—D) or a glutamic acid (Y—E).

4. The mouse according to claim 3, wherein said single mutation consists in the replacement of the tyrosine by a phenylalanine (Y—F).

5. An isolated germ cell or somatic cell from the mouse according to claim 1 or any progeny of said mouse containing the mutant LAT gene.

6. An isolated mutant mouse LAT gene encoding a mutant mouse LAT protein, wherein the sequence of the mutant mouse LAT protein comprises a single mutation of a tyrosine located at position 136 of the wild-type mouse LAT protein sequence, wherein the mutation is not a composite mutation of the tyrosine residues at positions 175, 195, and 235 of said wild-type mouse LAT protein sequence, wherein the single mutation of the tyrosine located at position 136 consists of a replacement with a residue preventing the association with the SH2 domain of proteins.

7. The mouse gene according to claim 6, wherein said single mutation consists in the replacement of the tyrosine by a phenylalanine (Y—F), an aspartic acid (Y—D) or a glutamic acid (Y—E).

8. The mouse gene according to claim 7, wherein said single mutation consists in the replacement of the tyrosine by a phenylalanine (Y—F).

9. The mutant mouse gene according to claim 6, wherein the sequence of the mutant mouse LAT gene is SEQ ID NO: 1.

10. The mutant mouse gene according to claim 6, wherein the mutant sequence encodes a mutant LAT protein comprising the mutated amino acid sequence of exon 7 (SEQ ID NO: 3).

11. A mouse whose genome comprises one allele of a mutant mouse LAT gene encoding a mutant mouse LAT protein, wherein the amino acid sequence of said mutant mouse LAT protein comprises a single mutation of a tyrosine located at position 136 of the wild-type mouse LAT protein sequence, wherein the mutation is not a composite mutation of the tyrosine residue at positions 175, 195 and 235 of said wild-type mouse LAT protein sequence, wherein the single mutation of the tyrosine located at position 136 consists of a replacement with a residue preventing the association with SH2 domain of proteins, wherein said mutant LAT gene replaces the endogenous wild-type LAT gene such that the mutant LAT gene is under the control of the regulatory regions of the endogenous mouse LAT gene, wherein the mouse is a carrier of a null allele of the endogenous LAT gene, and wherein the mouse has a phenotype of exaggerated TH2 cell differentiation.

12. The mouse according to claim 11, wherein said mutant LAT gene encodes coding for a mutant LAT protein comprising the mutated amino acid sequence of exon 7 (SEQ ID NO: 3).

13. The mouse according to claim 11, wherein said single mutation consists in the replacement of the tyrosine by a phenylalanine (Y—F), an aspartic acid (Y—D) or a glutamic acid (Y—E).

14. The mouse according to claim 13, wherein said single mutation consists in the replacement of the tyrosine by a phenylalanine (Y—F).

15. An isolated germ cell or somatic cell from the mouse according to claim 11 or any progeny of said mouse containing the mutated LAT gene.

* * * * *

SEQUENCE LISTING

<160> NUMBER OF SEQ ID NOS: 9

<210> SEQ ID NO 1
<211> LENGTH: 6307
<212> TYPE: DNA
<213> ORGANISM: Mus musculus

<400> SEQUENCE: 1

```
tatccatagt cccagactta acaggggctg tcaggtcacc ctgtgggtaa gtccctgtct    60
tctgagcttg gtaatctaga aggagggctg ctcttttctg agtgagctgg ttcagtatga   120
ctgtgactca ccgtggtccc ctggaagtcg ctctcccagt agttaagcct gggagctggg   180
ggcctgtggt gccctcagtg ccctcggtcc acacaggcct tggcagagcc tccttccagt   240
tctcccaccc gggcatgggg agggtaccgc gggcctggtt ggcacgtgtc tcctttccta   300
gtggacgggc tgcctcatcc tgcagcctta gaccttcct ccacacagtc cctctgcctc   360 ctccccttc ccacaactgg gtggggtga gtgggcaggg ggcaggctca gcctgctgag   420
cagcctgatg atttcctgcc ctcaccacag cttcctgtcg cacgcggtgg tgagcaggag   480
aggcaggcgg ggagcaagaa aggggcaggt acagctgggc acggggatcg tgcagctggt   540
agctggggca cgggccccag ctctggctct ggggcgagca cctttccaga gccaacactg   600
ctctcaactc agtccagcaa gagaggggag ccatccagcc ccgaaaggat acggctgcct   660
actgccgggc ggatcccagg ctggagcccg cttggtccca tacccctgct gccactctgt   720
ctcgaggggc tgcagtgcag cagggcctgt ggcaggtgct ctgcagatgg aagcagacgc   780
cttgagcccg gtggggctgg gcctcctgct gctgcccttc ttggtcacgc tcctggctgc   840
cctgtgcgtg cgctgccgtg agttgccagg taagtgggaa gctttgcgga actggatgat   900
gggtgggcgc tccattggat cctcatacc tccccagccc ctgcactctc cactgtccct   960
acctgggccc tgattgatgg tggggggcct gagtttcttt gtccctggtg caccccgatc  1020
ctgacttgtt ggatttcttt cctccagtct cctatgacag cacttccaca gagaggtgag  1080
tgggaagccc gtgtccctgt gtgtcttccc ttggttccac tcaagggttt ggggctgggg  1140
ccctcttggc cctgtaccca agctgtctct ttcctgccag tttgtaccca agaagcatcc  1200
tcatcaagcc acctcgtgag ttcagtgtct ctggccctcc tcgagggttt ttaagagtgt  1260
gcgtttgtcc ttgttcacct ttagctgtct gaagggctgt tccctggctt gggatgggga  1320
aagtgggagc cccatgtct gtctagggca tgttattttg gggtccattt gtccttcgag  1380
gccttgatgg ggggtgtctg gagccatccc tcaagcttca ttctgtgtcc tcagaaataa  1440
ccgtcccccg aacacctgct gtttcctacc ctctagtcac ttccttccca ccctgaggc  1500 agccagacct gctcccatc ccgtgagtat cccccaattc cgtcccttgg gtctactgtg  1560
cctctccacc ttctaggttg gggaggcgct ttttcctggt tgtcttgctc ccagagtcct  1620
acctagacgt aatctctgac ctttggcttc caggagatcc ccacagcccc ttgggggttc  1680
```

-continued

```
ccatcggatg ccatcttccc agcagaattc agatgatggt aagggtgtag ggcacaggag    1740
ggctttgggg aggatgtaca acctgagctg atccagtctt cttctccctc tctctttgaa    1800
gccaacagtg tggcaagcta cgagaaccag ggtgggtctg gggtctgggg tagtgggtgg    1860
ggtggggagg ctggacctgt ccaggtcgtg ttaactctcc tttctcacag agccagcctg    1920
taagaatgtg gatgcagatg aggatgaaga cgactatccc aacggcttcc tgtgagtggg    1980
tagaggagat ctgaccgtgg aagttgtgtg cccttatca acttctcgtt ccttcctttc    2040
ttccagagtg gtgctgcctg acagtagtcc tgctgccgtc cctgttgtct cctctgctcc    2100
tgtgcctagc aaccctgacc ttggagacag tgccttctct ggtgagtcag ctttctgtc    2160 tacctcctc tgccatgtgc tgccagctct ccactcttgc ctccctctca cctccgtgac    2220
gattgccgcc cttccatttc ctcctgtaga cgttgggctt cctgctcctc atcacttccg    2280
actgtcttgt ttttccttcc acctttgctc cttcgtctct gttgtctaag aaatttcctg    2340 actcttttg aaccctgcca ttgaaatttc atttctcggc tgggtgtgag ggcctacgat    2400
cccagcatca ggaggcagtg gcaggagggt tgaatttgag gctagcctgg gctacatagt    2460
gataccctct cttcgaaaac caaaacagca cgacgatcaa caaaaagaaa acaaaagaat    2520
ttatttctct tatctgaaag tcccctccc cttttttggc gtctcggttc tttttgtata    2580
gtacactgtt gtttcttgga agcaatatca tctaatgtat ctataagaac tttgattaca    2640
tagccgggtg gtggtggcgc acgcctttaa ttccagcact cgggaggcag aggcaggcgg    2700
atttctgagt tcaaggccag cctggtctac agagtgagtt ccaggacagc caggactaca    2760
cagagaaacc ctgtctcgaa aaacaaaac aaaacaaatt ttgattacag attgtttctc    2820
tctgtgtctc tatccctctc tggttctgcc cgtctctctg tatctctgcc cgtctctctg    2880
tatctctgcc cgtctctctg tatctctgcc cgtctctctg tatctctgcc cgtctctctg    2940
tatctctgcc cgtctctctg tatctatctc tgcccgtctc tctgtatctc tgcccgtctc    3000
tctgtatctc tgcccgtctc tctgtatctc tgcctgtctc tctcacacac actcactgaa    3060
gatttattct gcgtaccaca tggtcgttgt ttctcttggg ctgcttttct ctgctttggt    3120
ctttctcctt ccttgagctt ttctcaagtt ctggtgatct tcagttttct atcctcttat    3180
ctctgtatag catgagtatc ccttacctga aacacttcaa tacagatttg gaatatttta    3240
taaacatata ataaattctc ttggggatga aactcaagat aaaacatgta attaatttat    3300
tcatgtttta tacaaaccat atatgtaata tatacacagt ctgaagatag gttttttgttt    3360 tgtcttagtt ttattggcat agagcgtcat tgtatagtcc tggctgtcct ggaacttgat    3420
atctagacca ggtagactca aactcaaatt aaacgtgtag gttaccatgc tcggtcttta    3480
aggtagttct atgcaaattt taattaatct tttgtatgaa atagaagttt catgaaattt    3540
tccatttgtg gtatcgcacc agtatgaaaa ggttttggat ttcggaatat gatgaatttt    3600
ggagttttaa aaggaacacc caaccttctg tatttaccct agactattat gtctgtactc    3660
tggctctgtt tgtttggaga gagaatctca ctgtagagtc ctggctgccc tggaactcac    3720
tttgtagatt aagtatggcc tttaactcca gttgcctctg gcttctgagt tctgggatta    3780
tatggggtta aagacgtatc cctcttgttc cacttggttt ttgttgttgg tggtttgttt    3840
atttagcttt ttttttttca gttttctcc ctcaatacag cttttctcta tgtatccttg    3900
gctgtcctag acctcactct gtagaccagg ctgtccttga actcagaaat ctgcctgcct    3960
ctacctcctg agtgctggga ttaaaggcac gtgccaccac cacctggctc tcttgctcca    4020
```

-continued

```
tttgtaaccc actgactata caatgagtcc ccatgtcaat aaaaccaaga caaaacaaaa    4080
acctagcttc agactgcgta tatatgattt atataaacca tgcatgactt aattccgtgt    4140
aatttgtcat ttctctcctg aaccccagac tgtttgagtg atcccttcct tccatccgtc    4200
ctggtctctc gctcctcatt tcctggttat gtctgctgac ttttgctagg gatttaggga    4260
gccaatgcag caaacttgta atggtaaaag gatcattgct aggggcaaaa tgactcattt    4320
taatttcagt gagagactct gtctcaaaga actatggtgg aatggctaaa gcctccatgt    4380
gctcctgagt gtgtgcagtg cataacaca cagagaggta ctaagagaac tactgttaac    4440
tgaggagcaa ctctatgccc tcgtggtgtg tacagctcat tagacctcac agttcgtggg    4500
tgctctgctg accgtaccct cttccctcc tgtccctcac atctctctct gtactgtctc    4560
tctgtatggt atgctagagt ttatttattt acttaaattg atacagtctt gctgttgtga    4620
tgtccagtct gtcttgagct caagttagcg cctgcctccc gtcttctgag accacagcct    4680
ggctcaaggt tgctagtaat tggaacaacg gtagcacata tgtgtattgca ggctctgttt    4740
tacaatttat tgtttattcc tcactctagt ccttccaggc aggtcctgtt atgaacctca    4800
ttctacagac taggaaactg gggcagggag catttaggtg acttatctga ggttagatag    4860
ttgcttagtg ctgggactga ggtttgagcc agtgtatttg gctcagcttg tccacatgcc    4920
catacagaaa ccaggcaacc atgaaaccag aaagcaaaaa gctgtgtagc attgtgagtg    4980
acctttgtgg gcccaggaag gtgagggcaa gagctgataa cattgagaga ccaacaggtc    5040
tgagaagagg ggatgccaac tagaccaagt gtgccacttc ttcacagatc accaaggtct    5100
ctgcactctg agctccttgg agccctgctc tccagcctca ctgcctgagt cctgtattgt    5160
ctctgttcca ttcccccaga ggctctggtc ctggctctcc atccacctcc atggcccttg    5220
ccctgcccag gcttcttctc ccctcgcttt tcctgaatat tctctctata ttgtgagtct    5280
gcctgggggt tgtgttagga gacttagatg tctgagccgg gggtgggagg tgtctctggg    5340
gaacagtgcc tggctgagtg tctgctaata actgtactgc aatggctatt ctacagtgga    5400
gtcgtgtgaa gattacgtga atgttcctga gagtgaggag agcgcagagg cgtctctggg    5460
taggtgactc tgcactccat gcatggccca tagcctctcc ctaccctctg catggcctgc    5520
ccttcacacc actgtccctg ctggtctgtc cccacagatg ggagccggga gtatgtgaat    5580
gtgtccccag agcagcagcc agtgaccagg gctgagctgg gtgagtacca aggtgtaagg    5640
gggcagaggc tggggagcag ccttgagtag agagtctgta ggctgaacgg cagtctccct    5700
ctgttttttcc ctctcagcct ctgtgaactc ccaggaggtg gaagacgaag gagaagagga    5760
aggggtggat ggagaggaag ctcctgacta tgagaatctg caggagctta actgaaagcc    5820
tagtgagtgg tctctgtccc cgcccccacc ttgggccttc tctccaggac cccctcctg    5880
cctatcccca gtggttaggc acattctttg tggctctgga tacccgggtg gcttcatgac    5940
tgtcctccct gtctcccctg ccctgctgtg tttcagctgc agctgtctgt cctgaaactg    6000
gacttgctgg ggtgtcgcta agaggatccc atttgacctc tgccttgcca cagcctgaga    6060
atcttcccct aacttattgt cactttgggg tccagtctgt gtcccaata ttctgtacct    6120
tctgataaag cctgagaatg aatctggttc cagccagacc atgtcatgga ataaaggcca    6180
tgtgacataa agtcgtcgtt gtcttctttt tgttgttgct ggtgttgttg gtttgtttgt    6240
ttgtttaact gggacagggt cttgctatgt tgatcaaggc tggtcttgaa cctgtgggtg    6300
atcatcc                                                              6307
```

```
<210> SEQ ID NO 2
<211> LENGTH: 61
<212> TYPE: DNA
<213> ORGANISM: Mus musculus

<400> SEQUENCE: 2
agccagcctg taagaatgtg gatgcagatg aggatgaaga cgactatccc aacggcttcc      60
t                                                                     61

<210> SEQ ID NO 3
<211> LENGTH: 20
<212> TYPE: PRT
<213> ORGANISM: Mus musculus

<400> SEQUENCE: 3

Pro Ala Cys Lys Asn Val Asp Ala Asp Glu Asp Glu Asp Asp Tyr Pro
 1               5                  10                  15

Asn Gly Phe Leu
            20

<210> SEQ ID NO 4
<211> LENGTH: 24
<212> TYPE: DNA
<213> ORGANISM: artificial sequence
<220> FEATURE:
<223> OTHER INFORMATION: Description of Artificial sequence: primer

<400> SEQUENCE: 4
gtggcaagct acgagaacca gggt                                            24

<210> SEQ ID NO 5
<211> LENGTH: 24
<212> TYPE: DNA
<213> ORGANISM: artificial sequence
<220> FEATURE:
<223> OTHER INFORMATION: Description of Artificial sequence: primer

<400> SEQUENCE: 5
gacgaaggag caaaggtgga agga                                            24

<210> SEQ ID NO 6
<211> LENGTH: 22
<212> TYPE: DNA
<213> ORGANISM: artificial sequence
<220> FEATURE:
<223> OTHER INFORMATION: Description of Artificial sequence: primer

<400> SEQUENCE: 6
cccagaggca aaccctctga ag                                              22

<210> SEQ ID NO 7
<211> LENGTH: 24
<212> TYPE: DNA
<213> ORGANISM: artificial sequence
<220> FEATURE:
<223> OTHER INFORMATION: Description of Artificial sequence: primer

<400> SEQUENCE: 7
tcgaattcgc caatgacaag acgc                                            24

<210> SEQ ID NO 8
<211> LENGTH: 21
<212> TYPE: DNA
<213> ORGANISM: artificial sequence
<220> FEATURE:
```

-continued

```
<223> OTHER INFORMATION: Description of Artificial sequence: primer

<400> SEQUENCE: 8
ggagacttag atgtctgacc g                                              21

<210> SEQ ID NO 9
<211> LENGTH: 21
<212> TYPE: DNA
<213> ORGANISM: artificial sequence
<220> FEATURE:
<223> OTHER INFORMATION: Description of Artificial sequence: primer

<400> SEQUENCE: 9
gacagaccag cagggacagt g                                              21
```